US011842347B2

(12) United States Patent
Keen

(10) Patent No.: US 11,842,347 B2
(45) Date of Patent: Dec. 12, 2023

(54) AGE AND IDENTITY VERIFICATION SYSTEM

(71) Applicant: Altria Client Services LLC, Richmond, VA (US)

(72) Inventor: Jarrett Keen, Richmond, VA (US)

(73) Assignee: ALTRIA CLIENT SERVICES LLC, Richmond, VA (US)

(*) Notice: Subject to any disclaimer, the term of this patent is extended or adjusted under 35 U.S.C. 154(b) by 143 days.

(21) Appl. No.: 16/868,955

(22) Filed: May 7, 2020

(65) Prior Publication Data

US 2021/0350374 A1 Nov. 11, 2021

(51) Int. Cl.
*G06Q 20/40* (2012.01)
*G06Q 20/00* (2012.01)
(Continued)

(52) U.S. Cl.
CPC ....... *G06Q 20/4014* (2013.01); *G06K 7/1413* (2013.01); *G06K 7/1417* (2013.01);
(Continued)

(58) Field of Classification Search
CPC ............. G06Q 20/4014; G06Q 20/206; G06Q 50/265; G06K 7/1413; G06K 19/0723;
(Continued)

(56) References Cited

U.S. PATENT DOCUMENTS 8,689,804 B2 * 4/2014 Fernando ................ A24F 40/53
131/184.1
9,894,938 B2 2/2018 Vick et al.
(Continued)

FOREIGN PATENT DOCUMENTS

CA 2996380 A1 4/2017
WO WO-2019/126805 A1 6/2019
(Continued)

OTHER PUBLICATIONS

International Search Report and the Written Opinion of the International Searching Authority for corresponding international Application No. PCT/US2021/021804 dated Jun. 28, 2021.
(Continued)

*Primary Examiner* — Clifford B Madamba
(74) *Attorney, Agent, or Firm* — Harness, Dickey & Pierce, P.L.C.

(57) ABSTRACT

An age and/or identity verification system for reduced-risk devices (RRD) may include a RRD, the RRD initially in an inoperable state, an identity verification server configured to perform identity verification related to an adult consumer, and a computing device. The computing device may receive adult consumer identity information corresponding to the adult consumer from the adult consumer, receive the UID of the RRD, transmit the adult consumer identity information and the UID of the RRD to the identity verification server to perform identity verification of the adult consumer, receive results of the performed identity verification from the identity verification server, receive an encrypted key corresponding to the RRD based on the results of the performed identity verification of the adult consumer, and transmit the encrypted key to the RRD. The RRD may change the state of the RRD to an operable state based on the encrypted key.

20 Claims, 9 Drawing Sheets

(51) Int. Cl.
   *G06Q 30/00* (2012.01)
   *G06Q 50/26* (2012.01)
   *G06K 7/14* (2006.01)
   *G06K 19/07* (2006.01)
   *H04L 9/08* (2006.01)
   *H04L 9/40* (2022.01)
   *H04B 1/38* (2015.01)
   *G06Q 20/20* (2012.01)
   *G06Q 30/018* (2023.01)

(52) U.S. Cl.
   CPC ....... *G06K 19/0723* (2013.01); *G06Q 20/206* (2013.01); *G06Q 30/0185* (2013.01); *G06Q 50/265* (2013.01); *H04L 9/0819* (2013.01); *H04L 9/0866* (2013.01); *H04L 63/0428* (2013.01); *H04L 63/0884* (2013.01); *G06Q 2220/00* (2013.01); *H04B 1/38* (2013.01)

(58) Field of Classification Search
   CPC ....... H04L 9/0819; H04L 9/0866; H04B 1/38; A61M 2205/276; A61M 2205/3584; A61M 2205/609; A61M 15/06; A24F 40/65; G06F 21/31
   USPC .......................................................... 705/44
   See application file for complete search history.

(56) References Cited

U.S. PATENT DOCUMENTS

| | | |
|---|---|---|
| 2014/0060552 A1 | 3/2014 | Cohen |
| 2015/0136158 A1 | 5/2015 | Stevens et al. |
| 2015/0181945 A1* | 7/2015 | Tremblay ................ A24F 40/60 131/328 |
| 2016/0143361 A1 | 5/2016 | Juster et al. |
| 2016/0211693 A1* | 7/2016 | Stevens ................ A61M 11/042 |
| 2017/0119040 A1 | 5/2017 | Cameron |
| 2017/0185364 A1 | 6/2017 | Cameron |
| 2018/0020720 A1 | 1/2018 | Matischek et al. |
| 2018/0043114 A1 | 2/2018 | Bowen et al. |
| 2018/0093054 A1* | 4/2018 | Bowen ................ A61M 11/042 |
| 2021/0337878 A1* | 11/2021 | Gretton ................ A24F 40/10 |

FOREIGN PATENT DOCUMENTS

| | | | |
|---|---|---|---|
| WO | WO-2019126805 A1 * | 6/2019 | .......... G05B 19/042 |
| WO | WO-2020/006311 A1 | 1/2020 | |
| WO | WO-2020006311 A1 * | 1/2020 | ............. A24F 40/50 |

OTHER PUBLICATIONS

Palmer, 'Juul reveals plans for smart Bluetooth ecigs than use biometric data to prove a smoker's age and won't work near schools' Aug. 2018, retrieved at https://www.dailymail.co.uk/sciencetech/article-6021125/Juul-reveals-plans-smart-Bluetooth-e-cigs-use-biometric-data-prove-smokers-age.html.

Jeffries, 'Vapor Corp's biometric vaporizer unlocks with a fingerprint' Jan. 2014, retrieved at https://www.theverge.com/2014/1/7/5286400/vapor-corps-biometric-vaporizer-unlocks-with-a-fingerprint.

International Preliminary Report on Patentability for International Application No. PCT/US2021/021804 dated Nov. 17, 2022.

* cited by examiner

AGE AND IDENTITY VERIFICATION SYSTEM

BACKGROUND

Field

The present disclosure relates to systems, apparatuses, methods, and/or non-transitory computer readable media related to age and/or identity verification for reduced-risk or reduced-harm devices, such as heat-not-burn aerosol-generating devices, non-heated inhalable aerosol-generating devices, electronic vaping devices (e.g., e-vaping devices), etc.

Description

In various countries and other locations, the buying, selling, possession, and/or operation of tobacco-related, nicotine-related products, and/or non-nicotine related products, such as reduced-risk or reduced-harm products, are restricted based on the age of the consumer. Examples of reduced-risk (e.g., reduced-harm products) may include nicotine, or non-nicotine, heat-not-burn aerosol-generating devices, non-heated inhalable aerosol-generating devices, and/or electronic vaping devices (e.g., e-vaping devices), etc. For example, under United States federal law, only individuals who are twenty-one years of age or older are legally permitted to buy, possess, and/or consume or attempt to buy, possess, and/or consume tobacco-related and/or nicotine-related products. However, various states, cities, countries, and other jurisdictions, may have different minimum age requirements for the purchase, sales, possession, and/or consumption of tobacco-related products. Further, retailers, and other businesses that sell tobacco-related products to individuals, are legally required to verify that the purchaser of the tobacco-related product complies with the relevant minimum tobacco-product age regulations prior to the sale of the tobacco-related product to the individual.

SUMMARY

At least one embodiment relates to a computing device for verifying an identity of an adult consumer. In an example embodiment, the computing device may include a memory having computer readable instructions stored thereon, and at least one processor configured to execute the computer readable instructions. The at least one processor may be caused to receive adult consumer identity information corresponding to the adult consumer from the adult consumer, receive a unique ID (UID) of a reduced-risk device (RRD), transmit the adult consumer identity information to an identity verification server to perform identity verification of the adult consumer, receive results of the performed identity verification from the identity verification server, generate an encrypted key corresponding to the RRD based on the results of the performed identity verification of the adult consumer and the UID of the RRD, and transmit the encrypted key to the RRD, the encrypted key causing the RRD to change the state of the RRD based on the encrypted key.

At least one embodiment relates to a reduced-risk device (RRD) for use with an identity verification service, the RRD initially in an inoperable state. In an example embodiment, the RRD may include at least one transceiver configured to communicate with at least one computing device, a memory configured to store a private key corresponding to the RRD, and control circuitry configured to receive an encrypted key corresponding to the RRD from a computing device associated with an adult consumer, the encrypted key generated based on a unique ID (UID) corresponding to the RRD and results of an identity verification performed on the adult consumer by an identity verification server, decrypt the encrypted key using the private key, determine whether an identity of the adult consumer was successfully verified based on the decrypted key, and change the state of the RRD to an operable state based on results of the determining whether the identity of the adult consumer was successfully verified.

At least one embodiment relates to an identity verification system. In an example embodiment, the identity verification system may include a reduced-risk device (RRD) including a unique ID (UID) of the RRD and at least one transceiver, the RRD initially in an inoperable state, an identity verification server configured to perform identity verification related to an adult consumer, and a computing device. The computing device may be configured to receive adult consumer identity information corresponding to the adult consumer from the adult consumer, receive the UID of the RRD, transmit the adult consumer identity information and the UID of the RRD to the identity verification server to perform identity verification of the adult consumer, receive results of the performed identity verification from the identity verification server, receive an encrypted key corresponding to the RRD based on the results of the performed identity verification of the adult consumer, the encrypted key generated based on the UID of the RRD, and transmit the encrypted key to the RRD. The RRD may be further configured to change the state of the RRD to an operable state based on the encrypted key.

BRIEF DESCRIPTION OF THE DRAWINGS

The various features and advantages of the non-limiting example embodiments herein may become more apparent upon review of the detailed description in conjunction with the accompanying drawings. The accompanying drawings are merely provided for illustrative purposes and should not be interpreted to limit the scope of the claims. The accompanying drawings are not to be considered as drawn to scale unless explicitly noted. For purposes of clarity, various dimensions of the drawings may have been exaggerated.

Figure 1:
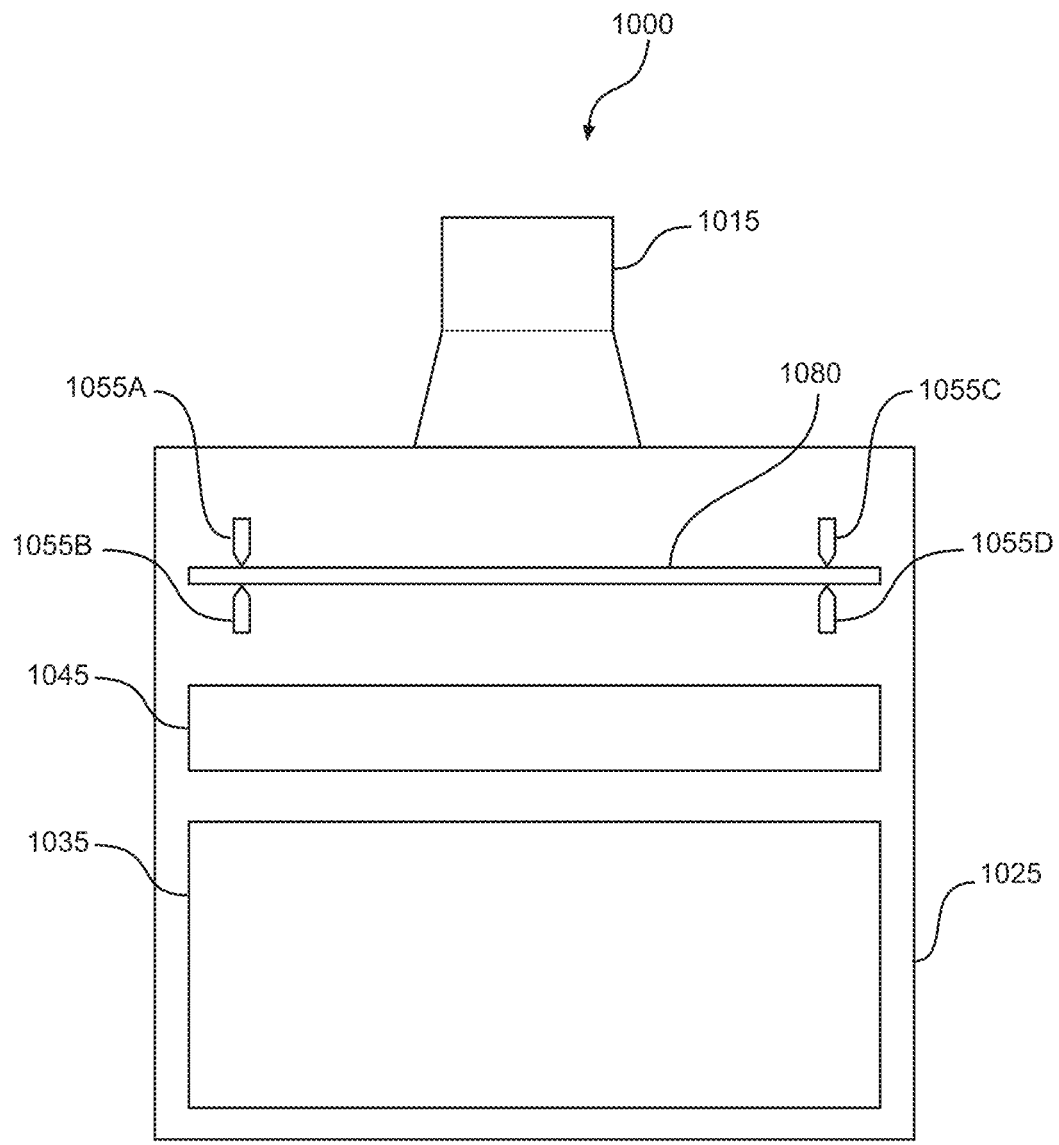
FIG. 1 is a schematic view of an example heat-not-burn aerosol-generating device according to at least one example embodiment.

It should be noted that these figures are intended to illustrate the general characteristics of methods and/or structure utilized in certain example embodiments and to supplement the written description provided below. These drawings are not, however, to scale and may not precisely reflect the precise structural or performance characteristics of any given example embodiment, and should not be interpreted as defining or limiting the range of values or properties encompassed by example embodiments.

DETAILED DESCRIPTION

Some detailed example embodiments are disclosed herein. However, specific structural and functional details disclosed herein are merely representative for purposes of describing example embodiments. Example embodiments may, however, be embodied in many alternate forms and should not be construed as limited to only the example embodiments set forth herein.

Accordingly, while example embodiments are capable of various modifications and alternative forms, example embodiments thereof are shown by way of example in the drawings and will herein be described in detail. It should be understood, however, that there is no intent to limit example embodiments to the particular forms disclosed, but to the contrary, example embodiments are to cover all modifications, equivalents, and alternatives falling within the scope of example embodiments. Like numbers refer to like elements throughout the description of the figures.

Various example embodiments relate to systems, apparatuses, methods, and/or non-transitory computer readable media related to age and/or identity verification for reduced-risk devices (e.g., reduced-harm devices, etc.). Examples of reduced-risk devices may include heat-not-burn aerosol-generating devices, non-heated inhalable aerosol-generating devices, electronic vaping devices (e.g., e-vaping devices), etc. A description of two example embodiments of reduced-risk devices are provided in connection with FIGS. 1-2, however the example embodiments of reduced-risk devices are not limited thereto, and may also include non-heated inhalable aerosol-generating devices, etc.

FIG. 1 is a schematic view of an example heat-not-burn aerosol-generating device according to at least one example embodiment. Referring to FIG. 1, a heat-not-burn aerosol-generating device 1000 may include a mouthpiece 1015 and a device body 1025, but is not limited thereto. A power supply 1035 and control circuitry 1045 may be disposed within the device body 1025 of the heat-not-burn aerosol-generating device 1000. According to at least one example embodiment, the heat-not-burn aerosol-generating device 1000 may include an I/O interface (not shown) and/or a network interface (not shown). The I/O interface may be a USB interface (e.g., a USB mini-cable interface), a power cable, etc. The network interface may be a Bluetooth transmitter (e.g., Bluetooth and/or Bluetooth Low Energy (LE), etc.), a NFC transmitter, a ZigBee transmitter, a WiFi transmitter, a cellular network transmitter, etc. Additionally, the heat-not-burn aerosol-generating device 1000 may also include a puff sensor (not shown) for detecting a puff, for example, by detecting an application of negative air pressure on the mouthpiece 1015, etc. In response to the detection of the puff and/or application of negative air pressure by the puff sensor, the control circuitry 1045 may be configured to control the supply of electric current to one or more heaters of the heat-not-burn aerosol-generating device 1000, etc.

The heat-not-burn aerosol-generating device 1000 is configured to receive a capsule 1080. The capsule 1080 is removable. According to at least some example embodiments, the capsule 1080 may include an aerosol-forming substrate (e.g., a pre-dispersion formulation, etc.) sandwiched in between first and second heaters. According to at least some example embodiments, the first and second heaters may be planar and may be formed of a material that heats up when an electric current is applied thereto. The heat-not-burn aerosol-generating device 1000 may also include a first electrode 1055*a*, a second electrode 1055*b*, a third electrode 1055*c*, and a fourth electrode 1055*d* configured to electrically contact the capsule 1080, but is not limited thereto. According to at least some example embodiments, the first electrode 1055*a* and the third electrode 1055*c* may electrically contact the first heater, while the second electrode 1055*b* and the fourth electrode 1055*d* may electrically contact the second heater. However, in non-limiting embodiments involving a capsule with only one heater, it should be understood that the first electrode 1055*a* and the third electrode 1055*c* (or the second electrode 1055*b* and the fourth electrode 1055*d*) may be omitted.

As used herein, the term "aerosol-forming substrate" refers to a material (or combination of materials) that may yield an aerosol. As referred to herein, an "aerosol" is any matter generated or outputted from any heat-not-burn aerosol-generating device according to any of the example embodiments disclosed herein. The material is in a solid form and is a predominant source of a compound (e.g., nicotine, a cannabinoid, etc.), wherein an aerosol including the compound is produced when the material is heated. The heating may be below the combustion temperature so as to produce an aerosol without involving a substantial pyrolysis of the aerosol-forming substrate or the substantial generation of combustion byproducts (if any). Thus, according to at least some example embodiments, pyrolysis does not occur during the heating and resulting production of aerosol. In other instances, there may be some pyrolysis and combustion byproducts, but the extent may be considered relatively minor and/or merely incidental. For example, once a heat-not-burn aerosol-generating device heats an aerosol-forming substrate to an aerosolization temperature, the aerosol-forming substrate may yield an aerosol. As used herein, the "aerosolization temperature" of an aerosol-forming substrate is the temperature at which the aerosol-forming substrate yields an aerosol, and is below the combustion temperature of the aerosol-forming substrate.

The aerosol-forming substrate may be a fibrous material. For instance, the fibrous material may be a botanical material. The fibrous material is configured to release a compound when heated. The compound may be a naturally occurring constituent of the fibrous material. For instance, the fibrous material may be plant material such as tobacco, and the compound released may be nicotine. The term "tobacco" includes any tobacco plant material including tobacco leaf, tobacco plug, reconstituted tobacco, compressed tobacco, shaped tobacco, or powder tobacco, and combinations thereof from one or more species of tobacco plants, such as *Nicotiana rustica* and *Nicotiana tabacum*.

Figure 2:
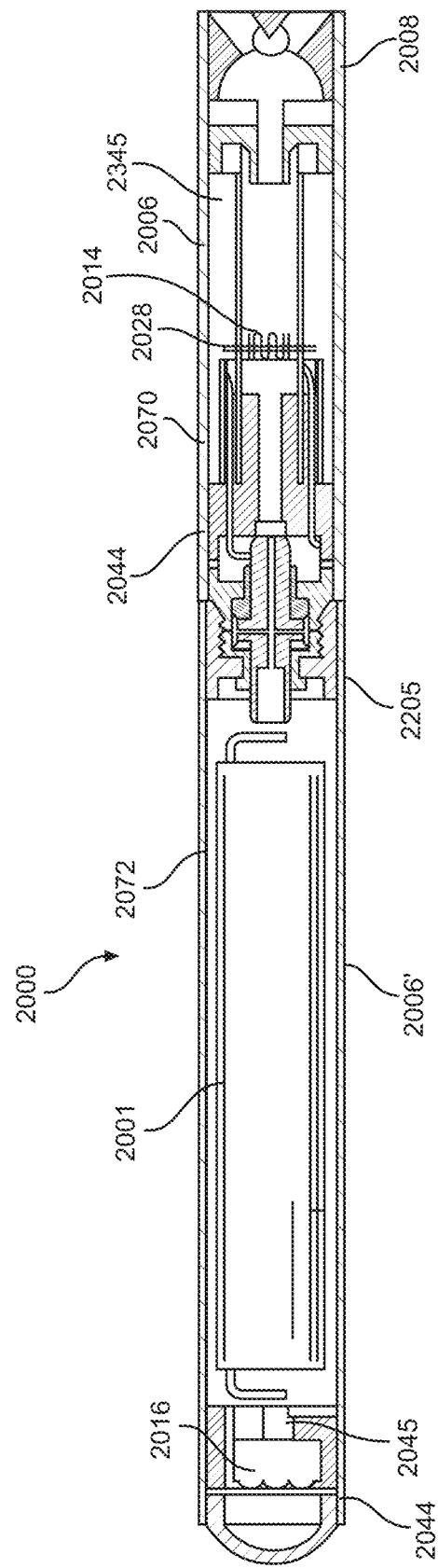
FIG. 2 is a cross-sectional view of an example e-vaping device according to at least one example embodiment.

FIG. 2 is a cross-sectional view of an example e-vaping device according to at least one example embodiment.

In at least one example embodiment, as shown in FIG. 2, an electronic vaping device (e-vaping device) 2000 may include a replaceable cartridge (or first section) 2070, and a reusable battery section (or second section) 2072, which may be coupled together at a threaded connector 2205. The first section 2070 (e.g., a dispersion generating article, a cartridge, a pod assembly, a pod, a capsule, etc.) may include a housing 2006 and the second section 2072 may include a second housing 2006'. The e-vaping device 2000 includes a mouth-end insert 2008. The first section 2070 may include a reservoir 2345 configured to contain an aerosol-forming substrate (e.g., a pre-dispersion formulation, etc.), such as a pre-vapor formulation, dry herbs, essential oils, etc., and at least one heater 2014 that may vaporize the aerosol-forming substrate, which may be drawn from the reservoir 2345 by a wick 2028.

In at least one example embodiment, the pre-vapor formulation is a material or combination of materials that may be transformed into a vapor. For example, the pre-vapor formulation may be a liquid, solid and/or gel formulation including, but not limited to, water, beads, solvents, active ingredients, ethanol, plant extracts, natural or artificial flavors, and/or vapor formers such as glycerin and propylene glycol. The pre-vapor formulation may include a nicotine compound or a non-nicotine compound.

In some example embodiments, the active ingredient(s) may be a nicotine compound or a non-nicotine compound. The nicotine compound may include tobacco, or may be a compound derived from tobacco, whereas the non-nicotine compound does not include tobacco, nor is the non-nicotine compound derived from tobacco. In at least one example embodiment, the non-nicotine compound is *cannabis*, or includes at least one *cannabis*-derived constituent. In at least one example embodiment, a *cannabis*-derived constituent includes at least one of a *cannabis*-derived cannabinoid (e.g., a phytocannabinoid, or a cannabinoid synthesized by a *cannabis* plant), at least one *cannabis*-derive terpene, at least one *cannabis*-derived flavonoid, or combinations thereof.

In at least one example embodiment, the pre-vapor formulation (either the nicotine or non-nicotine versions) includes at least one flavorant. In at least one example embodiment, the at least one flavorant may be at least one of a natural flavorant, an artificial flavorant, or a combination of a natural flavorant and an artificial flavorant. For instance, the at least one flavorant may include menthol, wintergreen, peppermint, cinnamon, clove, combinations thereof, and/or extracts thereof. In addition, flavorants may be included to provide herb flavors, fruit flavors, nut flavors, liquor flavors, roasted flavors, minty flavors, savory flavors, combinations thereof, and any other desired flavors.

In at least one example embodiment, the non-nicotine pre-vapor formulation at least one flavorant includes volatile *cannabis* flavor compounds (flavonoids). In at least one example embodiment, the at least one flavorant of the non-nicotine pre-vapor formulation includes flavor compounds instead of, or in addition to, the *cannabis* flavor compounds.

In at least one example embodiment, the non-nicotine compound may be a medicinal plant, or a naturally occurring constituent of the plant that has a medically-accepted therapeutic effect. The medicinal plant may be a *cannabis* plant, and the constituent may be at least one *cannabis*-derived constituent. Cannabinoids (phytocannabinoids) are an example of a *cannabis*-derived constituent, and cannabinoids interact with receptors in the body to produce a wide range of effects. As a result, cannabinoids have been used for a variety of medicinal purposes. *Cannabis*-derived materials may include the leaf and/or flower material from one or more species of *cannabis* plants, or extracts from the one or more species of *cannabis* plants. In at least one example embodiment, the one or more species of *cannabis* plants includes *Cannabis sativa, Cannabis indica*, and *Cannabis ruderalis*. In some example embodiments, the non-nicotine pre-vapor formulation includes a mixture of *cannabis* and/or *cannabis*-derived constituents that are, or are derived from, 60-80% (e.g., 70%) *Cannabis sativa* and 20-40% (e.g., 30%) *Cannabis* indica.

Examples of *cannabis*-derived cannabinoids include tetrahydrocannabinolic acid (THCA), tetrahydrocannabinol (THC), cannabidiolic acid (CBDA), cannabidiol (CBD), cannabinol (CBN), cannabicyclol (CBL), cannabichromene (CBC), and cannabigerol (CBG). Tetrahydrocannabinolic acid (THCA) is a precursor of tetrahydrocannabinol (THC), while cannabidiolic acid (CBDA) is precursor of cannabidiol (CBD). Tetrahydrocannabinolic acid (THCA) and cannabidiolic acid (CBDA) may be converted to tetrahydrocannabinol (TI-IC) and cannabidiol (CBD), respectively, via heating. In at least one example embodiment, heat from the heater 60 may cause decarboxylation to convert tetrahydrocannabinolic acid (THCA) in the non-nicotine pre-vapor formulation to tetrahydrocannabinol (THC), and/or to convert cannabidiolic acid (CBDA) in the non-nicotine pre-vapor formulation to cannabidiol (CBD).

In instances where both tetrahydrocannabinolic acid (THCA) and tetrahydrocannabinol (THC) are present in the non-nicotine pre-vapor formulation, the decarboxylation and resulting conversion will cause a decrease in tetrahydrocannabinolic acid (THCA) and an increase in tetrahydrocannabinol (THC). At least 50% (e.g., at least 87%) of the tetrahydrocannabinolic acid (THCA) may be converted to tetrahydrocannabinol (THC), via the decarboxylation process, during the heating of the non-nicotine pre-vapor formulation for purposes of vaporization. Similarly, in instances where both cannabidiolic acid (CBDA) and cannabidiol (CBD) are present in the non-nicotine pre-vapor formulation, the decarboxylation and resulting conversion will cause a decrease in cannabidiolic acid (CBDA) and an increase cannabidiol (CBD). At least 50% (e.g., at least 87%) of the cannabidiolic acid (CBDA) may be converted to cannabidiol (CBD), via the decarboxylation process, during the heating of the non-nicotine pre-vapor formulation for purposes of vaporization.

Referring again to FIG. 2, during vaping, pre-vapor formulation, or the like, may be transferred from the reservoir 2345 to the proximity of the heater 2014 via capillary action of the wick 2028. The wick 2028 may include at least a first end portion and a second end portion, which may extend into opposite sides of the reservoir 2345. The heater 2014 may at least partially surround a central portion of the wick 2028 such that when the heater 2014 is activated, the pre-vapor formulation (or the like) in the central portion of the wick 2028 may be vaporized by the heater 2014 to form a vapor.

In at least one example embodiment, the heater 2014 may include a wire coil which at least partially surrounds the wick 2028. The wire may be a metal wire and/or the heater coil may extend fully or partially along the length of the wick 2028. The heater coil may further extend fully or partially around the circumference of the wick 2028. In some example embodiments, the heater coil 2014 may or may not be in contact with the wick 2028.

In at least one example embodiment, the heater 2014 may heat pre-vapor formulation (or the like) in the wick 2028 by thermal conduction. Alternatively, heat from the heater 2014 may be conducted to the pre-vapor formulation (or the like) by means of a heat conductive element or the heater 2014 may transfer heat to the incoming ambient air that is drawn through the e-vaping device 2000 during vaping, which in turn heats the pre-vapor formulation (or the like) by convection.

It should be appreciated that, instead of using a wick 2028, the heater 2014 may include a porous material which incorporates a resistance heater formed of a material having an electrical resistance capable of generating heat quickly.

In at least one example embodiment, as shown in FIG. 2, the second section 2072 of the e-vaping device 2000 may include a puff sensor 2016 (e.g., a pressure sensor, a flow sensor, etc.) responsive to air drawn into the second section 2072 via an air inlet port 2044a adjacent a free end or tip of the e-vaping device 2000. The second section 2072 may also include a power supply 2001.

Additionally, the second section 2072 of the e-vaping device 2000 may include control circuitry 2045 and a battery monitoring unit (BMU) (not shown). In some example embodiments, the second section 2072 may also include an external device input/output interface (not shown) and/or a network interface (not shown). The I/O interface may be a USB interface (e.g., a USB mini-cable interface), a power cable, etc. The network interface may be a Bluetooth transmitter (e.g., Bluetooth and/or Bluetooth Low Energy (LE), etc.), a NFC transmitter, a ZigBee transmitter, a WiFi transmitter, a cellular network transmitter, etc.

The control circuitry 2045 includes a microprocessor, a non-transitory computer-readable storage medium, a heater control circuitry, and/or a charge control circuitry, etc., and may be connected to the puff sensor 2016.

The control circuitry 2045 performs features of the second section 2072, as well as the entire e-vaping device 2000, such as controlling the heater, interfacing with an external charger and monitoring the pressure within the e-vaping device 2000 to determine whether negative air pressure has been applied. Moreover, the control circuitry 2045 may determine whether a positive pressure has been applied for a threshold time. In such an instance, the control circuitry 2045 may place the e-vaping device 2000 in a disabled and/or hibernation mode (reduced power consumption and/or preventing activation).

The control circuitry 2045 may be processing and/or control circuitry, hardware executing software, or any combination thereof. When the control circuitry 2045 is hardware, such existing hardware may include one or more Central Processing Units (CPUs), one or more microcontrollers, one or more arithmetic logic units (ALUs), digital signal processors (DSPs), application-specific-integrated-circuits (ASICs), field programmable gate arrays (FPGAs), one or more System-on-Chips (SoCs), one or more programmable logic units (PLUs), one or more microprocessors, computers, or any other device or devices capable of responding to and executing instructions in a defined manner, configured as special purpose machines to perform the functions of the control circuitry 2045.

In the event where the control circuitry 2045 is at least one processor executing software (e.g., computer readable instructions), the control circuitry 2045 is configured as a special purpose machine to execute the software, stored in the non-transitory computer-readable storage medium, to perform the functions of the control circuitry 2045.

Upon completing the connection between the first section 2070 and the second section 2072, the power supply 2001 may be electrically connectable with the heater 2014 of the first section 2070 upon actuation of the puff sensor 2016. Air is drawn primarily into the first section 2070 through one or more air inlets 2044, which may be located along the housing or at the connector 2205.

The power supply 2001 may include a battery arranged in the e-vaping device 2000. The power supply 2001 may be a Lithium-ion battery or one of its variants, for example a Lithium-ion polymer battery. Alternatively, the power supply 2001 may be a nickel-metal hydride battery, a nickel cadmium battery, a lithium-manganese battery, a lithium-cobalt battery or a fuel cell, etc.

In at least one example embodiment, the power supply 2001 may be rechargeable and may include circuitry configured to allow the battery to be chargeable by an external charging device. To recharge the e-vaping device 2000, an USB mini-charger or other suitable charger assembly may be used in connection with a charging interface (not shown).

In at least one example embodiment, the first section 2070 may be replaceable. In other words, once the pre-vapor formulation, or other contents, of the cartridge is depleted, only the first section 2070 may be replaced. An alternate arrangement may include an example embodiment where the entire e-vaping device 2000 may be disposed once the reservoir 2345 is depleted. Additionally, according to at least one example embodiment, the first section 2070 may also be configured so that the contents of the cartridge may be re-fillable.

While FIGS. 1 to 2 depict example embodiments of reduced-risk or reduced-harm devices, the example embodiments are not limited thereto, and may include additional and/or alternative reduced-risk or reduced-harm devices, such as non-heated inhalable devices, or non-nicotine versions of the reduced-risk or reduced-harm devices, etc. Further, the hardware configurations for the reduced-risk device are not limited to any single embodiment, and other hardware configurations that may be suitable for the purposes demonstrated may be used as well. For example, the reduced-risk device may include a plurality of additional or alternative elements and/or additional or alternative functions, such as additional elements and/or functions discussed in connection with FIGS. 3 to 4B, etc., as well as additional or alternative heating elements, reservoirs, batteries, etc. Additionally, while FIGS. 1 to 2 depict the example embodiment of the reduced-risk devices as being embodied in two separate housing elements, additional example embodiments may be directed towards reduced-risk devices arranged in a single housing, and/or in more than two housing elements.

For example, the non-nicotine versions of the reduced-risk or reduced-harm device may generate a dispersion (e.g., an aerosol, a vapor, etc.) from a non-nicotine pre-dispersion formulation (e.g., an aerosol-generating substrate, a pre-vapor formulation, etc.) including a non-nicotine compound. In an example embodiment, the non-nicotine pre-dispersion formulation neither includes tobacco nor is derived from tobacco. A non-nicotine compound of the non-nicotine pre-vapor formulation may be part of, or included in a liquid or a partial-liquid that includes an extract, an oil, an alcohol, a tincture, a suspension, a dispersion, a colloid, a general non-neutral (slightly acidic or slightly basic) solution, or combinations thereof. During the preparation of the non-nicotine pre-dispersion formulation, the non-nicotine compound may be infused into, comingled, or otherwise combined with the other ingredients of the non-nicotine pre-dispersion formulation.

Figure 3:
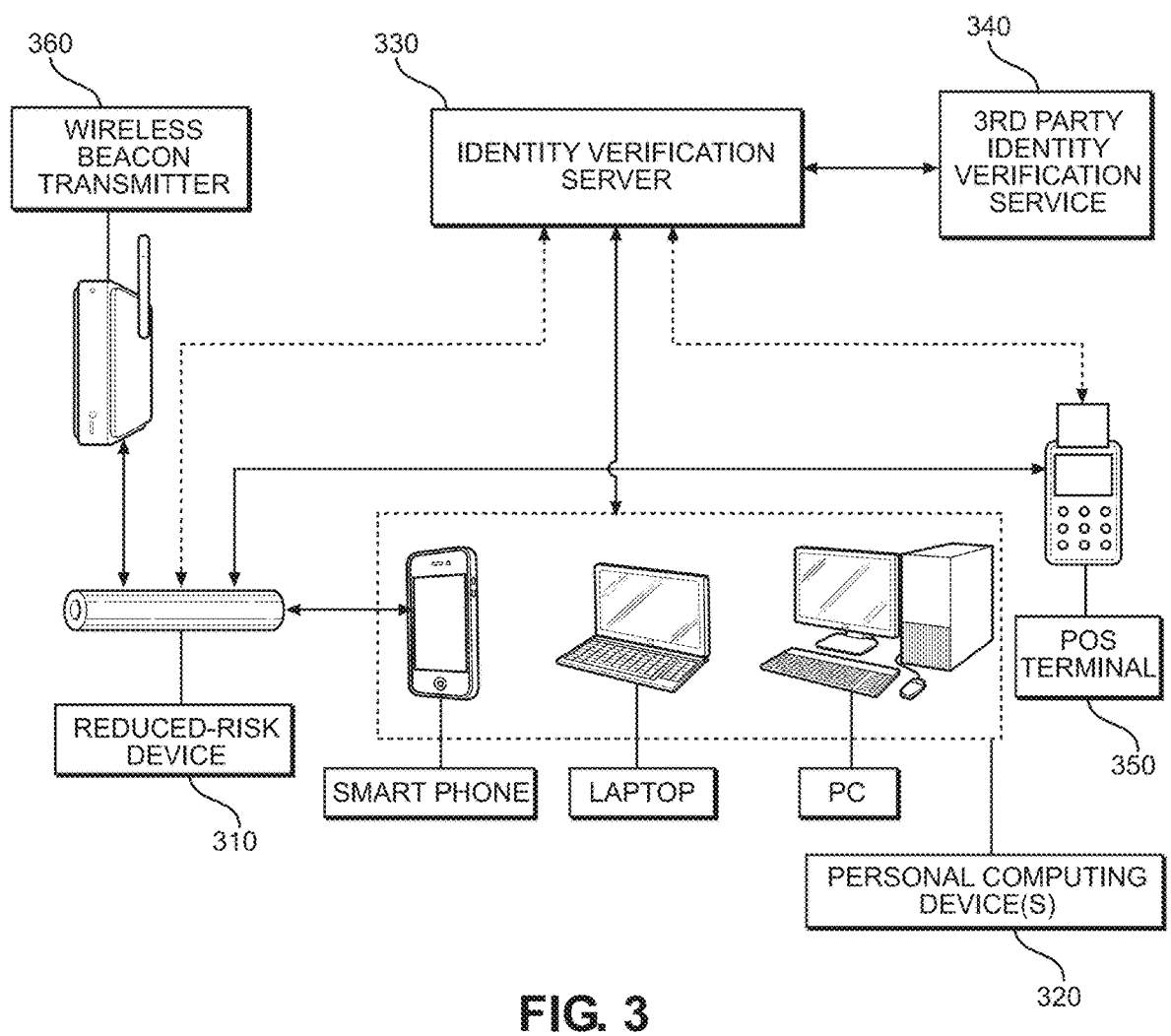
FIG. 3 is a block diagram illustrating various elements of an identity verification system including a reduced-risk device, a personal computing device, and an identity verification server according to at least one example embodiment.

FIG. 3 is a block diagram illustrating various elements of an identity verification system including a reduced-risk (and/or reduced-harm) device, a personal computing device, and an identity verification server according to at least one example embodiment.

Referring to FIG. 3, according to at least one example embodiment, an identity verification system may include at least one reduced-risk device 310 (e.g., a heat-not-burn aerosol generating device, a non-heated inhalable device, an e-vaping device, etc.), at least one personal computing device 320 associated with one or more adult consumers, and/or an identity verification server 330, etc., but the example embodiments are not limited thereto and there may be a greater or lesser number of each individual element in the system and/or other additional elements included in the identity verification system according to other example embodiments. According to some example embodiments, the reduced-risk device 310 may be a nicotine reduced-risk device or a non-nicotine reduced-risk device, etc. Additionally, in some example embodiments, the identity verification system may also include a third-party identity verification service 340 and/or a point-of-sale (POS) terminal 350, a wireless beacon transmitter 360, etc.

According to some example embodiments, the personal computing device 320 may be a smartphone, a mobile phone, a tablet, a laptop, a personal computer (PC), a personal digital assistant (PDA), a wearable device, a virtual reality (VR) and/or augmented reality (AR) device, an Internet-of-Things (IoT) device, a voice assistant device, etc., but the example embodiments are not limited thereto. The personal computing device 320 may be associated with an adult consumer who intends to operate the reduced-risk device 310 and/or operate the reduced-risk device 310 in conjunction with a new and/or replacement element of the reduced-risk device 310 (not shown). Examples of the new and/or replacement element include a new and/or replacement dispersion generating article (e.g., a cartridge, a capsule, a heat-stick, etc.) for the reduced-risk device 310, power supply section for the reduced-risk device 310, etc.

The personal computing device 320 may operate an identity verification software application (e.g., an identity verification app, a reduced-risk device application, etc.) to receive information related to the reduced-risk device 310 and/or the element(s) of the reduced-risk device, input identity verification information related to the identity of the adult consumer, receive identity verification results from the identity verification server 330, and/or transmit an encrypted key to the reduced-risk device 310 to enable the operation of the reduced-risk device 310 and/or individual elements of the reduced-risk device, but the example embodiments are not limited thereto. According to some example embodiments, the personal computing device 320 may manually and/or automatically lock an unlocked the reduced-risk device 310 based on input received from the adult consumer through the identity verification software application (e.g., app) installed on the personal computing device 320 and/or a disconnection of a communication session between the reduced-risk device 310 and the personal computing device 320.

Additionally, the personal computing device 320 may be a device that is operated by the retailer and/or business to facilitate the verification of an adult consumer during the purchasing of the reduced-risk device and/or elements of the reduced-risk device. For example, the retailer and/or business may use a POS terminal 350, an age/identity verification kiosk (e.g., stand-alone kiosk), and/or other dedicated device to verify the identity of the adult consumer and/or to enable the operation of the reduced-risk device 310 and/or elements of the reduced-risk device, etc.

The reduced-risk device 310 and/or the element(s) of the reduced-risk device 310 may initially be in a "locked" state (e.g., age/identity lock state may be engaged, disabled state, etc.) which renders the reduced-risk device 310 and/or the reduced-risk device elements in an inoperable state until the reduced-risk device 310 and/or reduced-risk device elements enter into an "unlocked" state (e.g., the age/identity lock state may be disengaged, in an enabled state, etc.). For example, prior to the legal sale of the reduced-risk device 310 from a retailer and/or business, the reduced-risk device 310 may be in an initial locked or disabled state, wherein the control circuitry (e.g., a controller, a processor, etc.) of the reduced-risk device 310 may disable the generation of vapor using the reduced-risk device 310 and/or may disable the operation of the power supply of the reduced-risk device 310, etc., by setting a locked state flag (e.g., a locked state setting, an age/identity verification lock setting, disable setting, etc.) in the lock control routine 523 of the memory 520.

The reduced-risk device 310 and/or reduced-risk device elements may be placed in the locked or disabled state at the time of manufacture (e.g., have the age/identity lock flag set in the memory), but the example embodiments are not limited thereto. For example, the reduced-risk device 310 may be temporarily unlocked or enabled through a successful age and/or identity verification of the adult consumer, and after a desired period of time (or other criterion) has occurred, the reduced-risk device 310 may re-enter the locked or disabled state (e.g., have the age/identity lock flag set).

Additionally, upon the detection of negative air pressure (e.g., a puff) on the mouthpiece of the reduced-risk device 310 by the puff sensor 595, the control circuitry 510 of the reduced-risk device 310 may determine whether the reduced-risk device 310 is in the "locked" state (e.g., determine whether the age/identity locked state flag, setting, etc., has been set) in order to determine whether to enable the operation of the heater 540 in response to the detected negative air pressure. If the reduced-risk device is in the locked state (e.g., the lock flag is set), the control circuitry 510 does not allow (e.g., prevents, prohibits, disables, etc.) the powering of the heater 540 by the power supply 530. If the lock flag is not set, the control circuitry 510 allows (e.g., enables, permits, etc.) the powering of the heater 540 by the power supply 530.

The reduced-risk device 310 and/or the elements of the reduced-risk device may include a unique identifier (UID) on the reduced-risk device 310 and/or on the individual element(s) of the reduced-risk device that uniquely identifies the item. For example, the UID of the reduced-risk device 310 may be used during the identity verification process of the individual purchasing the reduced-risk device 310, and the UID may also be used to associate the reduced-risk device 310 with an account of the individual on a database for verification purposes, such as the verification history of a particular reduced-risk device and/or element(s) of a reduced-risk device (collectively referred to as the reduced-risk device hereinafter). A personal UID corresponding to the adult consumer may be associated with the individual's account as well.

The personal computing device 320 may be used to capture and/or receive the UID of the reduced-risk device 310 and/or the UID of the individual element(s) of the reduced-risk device. For example, a camera included in the personal computing device 320 may be used to capture an image of the UID of the reduced-risk device 310, a sensor (e.g., a RFID sensor, an NFC sensor, an IR reader, etc.)

included in the personal computing device 320 may be used to sense/detect/read the UID of the reduced-risk device 310, and/or the individual operating the personal computing device 320 may manually input the UID of the reduced-risk device 310 into verification software operating on the personal computing device 320. Additionally, according to some example embodiments, the personal computing device 320 may establish a wired and/or wireless communication connection (e.g., communication via a USB connection, WiFi connection, Bluetooth connection, NFC connection, etc.) with the reduced-risk device 310, and may receive the UID of the reduced-risk device 310 and/or the UID of the element(s) of the reduced-risk device via the communication connection, etc.

Further, once a connection has been established between the personal computing device 320 and the reduced-risk device 310, the personal computing device 320 may store location information related to the personal computing device 320 and/or the reduced-risk device 310 at the time of the connection establishment and/or at the time when the connection is disconnected. The location information may be obtained from the GPS sensor 590 (and/or other location sensor) included in the reduced-risk device 310, the GPS sensor 460 (and/or other location sensor) included in the personal computing device 320, and/or may be determined based on other information associated with the reduced-risk device 310 and/or the personal computing device 320, such as location information lookup based on the IP address of the personal computing device 320, WiFi fingerprint analysis of the WiFi signals detected by the personal computing device 320, cellular triangulation of the personal computing device 320, etc. Once the location information has been obtained, the location information may be stored in the RRD profile information 425 of the memory 420 of the personal computing device 320. Moreover, the location information of the reduced-risk device 310 and/or the personal computing device 320 may be periodically refreshed using the GPS sensor 590, the GPS sensor 460, etc., while the reduced-risk device 310 is connected to the personal computing device 320. Additionally, according to some example embodiments, the location information may be transmitted to the identity verification server 330 and stored in association with the adult consumer's profile in the verification information database 623. The location information may be used to determine the last known location of the reduced-risk device 310 in the event that the adult consumer loses and/or misplaces the reduced-risk device 310, etc.

In addition, the adult consumer may use the reduced-risk device software to enable a "find-my-device"-type feature, wherein an adult consumer may use the reduced-risk device software to determine the last known location of a reduced-risk device. According to at least one example embodiment, the adult consumer may operate the reduced-risk device software (e.g., press a GUI button to initiate the "find-my-device" feature, etc.) to transmit a find-my-device instruction (e.g., a message, an indication, etc.) to the reduced-risk device 310 over a wireless connection (e.g., Bluetooth connection, NFC connection, WiFi connection, etc.) and/or a wired connection. If the reduced-risk device 310 is connected to the personal computing device 320 via the wireless connection and/or wired connection, the reduced-risk device 310 may receive the transmitted find-my-device instruction. Additionally, the reduced-risk device 310 may transmit an acknowledgement message in response to the transmitted find-my-device instruction, thereby allowing the personal computing device 320 to initiate a timer, a countdown, etc., and/or display a timer, a countdown, etc., on the GUI of the reduced-risk device software to indicate the length of time that the find-my-device operation has been in effect (and/or the time remaining in the desired time period for the find-my-device operation). If the timer expires prior to the adult consumer locating the reduced-risk device 310, the adult consumer may re-initiate the find-my-device operation using the GUI of the reduced-risk device software.

Upon receiving the find-my-device instruction, if the reduced-risk device 310 is in a low-power mode (and/or a sleep mode, an off state, etc.), the reduced-risk device 310 will enter a normal-power mode (and/or an on mode, a performance mode, a wake state, etc.) in response to the received find-my-device instruction. In the event that the reduced-risk device 310 is already in the normal-power mode or the reduced-risk device 310 has entered the normal-power mode in response to the received find-my-device instruction, the reduced-risk device 310 will display and/or emit at least one responsive indication in response to the received find-my-device instruction. For example, the responsive indication may be the flashing of a LED light(s) on the reduced-risk device 310, the display of a message on the reduced-risk device 310, emitting a sound through a speaker of the reduced-risk device 310, a haptic feedback (e.g., vibration, etc.) produced by the reduced-risk device 310, etc., in order to draw the adult consumer's attention to the current location of the reduced-risk device 310. However, the example embodiments are not limited thereto, and the responsive indication may be any equivalent indication performable by the reduced-risk device 310.

According to some example embodiments, the responsive indication may be produced at levels that increase the likelihood that the adult consumer will find the reduced-risk device 310, such as displaying the LED lights at maximum brightness, emitting a sound on the speaker at maximum volume, and/or producing a haptic feedback at a maximum vibration level, etc. Further, the responsive indication may be a combination of indications (e.g., a flashing LED light and an emitted sound, etc.) and/or may be produced based on a desired pattern (e.g., light pattern, sound pattern, and/or haptic feedback pattern, etc.), and additionally, the responsive indication may be performed in a loop for a desired number of sequences and/or a desired time period, etc. The reduced-risk device 310 may produce the responsive indication for a desired period of time (e.g., 750 ms, etc.) before returning to its previous state (e.g., the state the reduced-risk device 310 was in prior to receiving the indication from the personal computing device 320).

Once the adult consumer locates the reduced-risk device 310, the adult consumer may cancel the production of the responsive indication on the reduced-risk device 310 by operating the reduced-risk device 310, for example, by engaging an I/O device of the reduced-risk device 310, engaging a UI button on the reduced-risk device 310, engaging the puff sensor of the reduced-risk device 310, etc. The cancellation of the responsive indication on the reduced-risk device 310 may initiate the transmission of a cancellation message to the personal computing device 320 over the connection that indicates that the adult consumer has located the reduced-risk device 310 and/or cancelled the find-my-device operation. The personal computing device 320 may display a status indication on the GUI of the reduced-risk device software based on the received cancellation message.

Additionally, the adult consumer may cancel the "find-my-device" operation using the personal computing device 320 through the GUI of the reduced-risk device software. For example, the GUI of the reduced-risk device software may display a UI element that initiates the cancelling of the "find-my-device" operation by causing the personal computing device 320 to transmit a cancellation instruction to the reduced-risk device 310. Upon receiving the cancellation instruction, the reduced-risk device 310 may cancel (e.g., stop) the production of the responsive indication and return to the reduced-risk device's previous state.

According to at least one example embodiment, if the reduced-risk device 310 is not connected to the personal computing device 320, the personal computing device 320 may display the stored location information (e.g., last known location information) corresponding to the last location that the reduced-risk device 310 connected to the personal computing device 320 and/or the last location where the connection between the reduced-risk device 310 and the personal computing device 320 was terminated on the GUI of the reduced-risk device software, thereby indicating the last known location of the reduced-risk device 310. Additionally, according to some example embodiments, the GUI of the reduced-risk device software may also display a map with a location indication (e.g., a marker, an avatar associated with the reduced-risk device, etc.) corresponding to the last known location information of the reduced-risk device 310, as well as the stored location information. Further, the GUI of the reduced-risk device software may also display additional information associated with the location information that may be useful to the adult consumer, such as a mailing address associated with the location information, a business name associated with the location information, a phone number associated with the location information, photos associated with the location information, etc. Moreover, the GUI of the reduced-risk device software may display the last known location information, the map view corresponding to the last known location information, and/or the additional information associated with the location information, etc., even when the reduced-risk device 310 and the personal computing device 320 have an established connection as discussed above.

According to some example embodiments, the adult consumer may also initiate an identity verification request to unlock the reduced-risk device 310 from the personal computing device 320 using the reduced-risk device software, and may also input the adult consumer's identity verification information into the personal computing device 320 via the GUI of the reduced-risk device software. The personal computing device 320 may transmit the identity verification information to the identity verification server 330 to verify the age and/or identity of the adult consumer, as well as other information related to the identity verification request, such as location information corresponding to the location of the personal computing device 320 and/or the reduced-risk device 310, etc., date information corresponding to the date of the identity verification request, time information corresponding to the time of the identity verification request, etc. The personal computing device 320 may communicate with the identity verification server over a wired and/or wireless network, such as the Internet, an intranet, a wide area network, a local area network, a personal area network, a cellular data network, etc., but the example embodiments are not limited thereto.

The identity verification information may be personal information associated with the adult consumer identity, such as the adult consumer's name, date of birth, current address, past addresses, phone number, place of birth, social security number, relatives' names, etc., account information associated with the adult consumer, such as a username and password, biometric information of the adult consumer, such as the adult consumer's fingerprint information, retina information, voice information, facial characteristics information, heartbeat information, etc., social networking service (SNS) information, instant messaging service account information, etc., but the example embodiments are not limited thereto. The identity verification information may also include other information which may specifically identify the adult consumer, such as information related to an individual's employment history, educational history, banking history, places that the individual has lived, names of relatives, etc. However, the example embodiments are not limited thereto, and other identity verification information specific to the adult consumer may be used.

Additionally, according to some example embodiments, the identity verification server may transmit to the personal computing device 320 identity verification challenge questions which require the adult consumer to successfully answer questions specific to the adult consumer's identity. For example, the identity verification challenge questions may include questions related to the adult consumer's mother's maiden name, place of birth, individual's employment history, educational history, banking history, places that the individual has lived, names of relatives, etc. The identity verification challenge questions may be questions that the adult consumer has previously created and/or submitted answers for, or may be questions and answers collected by a third party and/or external identity verification service 340 based on public records available regarding the adult consumer. Additionally, the identity verification challenge question may be a requirement for the adult consumer to provide biometric information (e.g., fingerprints, facial scan, retina scan, voice identification, etc.) that matches previously provided biometric information of the adult consumer. However, the example embodiments are not limited thereto and the identity verification challenge questions may take other equivalent forms that provide accurate verification of a person's identity.

According to some example embodiments, the identity verification server 330 may optionally connect to the third party identity verification service 340 over a network, request the identity verification challenge questions and/or answers corresponding to the adult consumer from the third party identity verification service 340, and transmit the identity verification challenge questions to the personal computing device 320 of the adult consumer. Once the adult consumer provides his or her answers to the identity verification challenge questions, the personal computing device 320 may transmit the answers to the identity verification server 330, and the identity verification server 330 may determine whether the answers input by the adult consumer are correct based on the answers received from the third party identity verification service 340, and/or transmit the answers input by the adult consumer to the third party identity verification service 340 for verification.

Once the answers have been verified by the identity verification server 330 and/or the third party identity verification service 340, a verification result is transmitted to the personal computing device 320 by the identity verification server 330. The personal computing device 320 may determine whether the verification result indicates that the adult consumer's identity was properly verified by the identity verification server 330 (and/or the third party verification service 340), and the adult consumer is legally allowed to operate the reduced-risk device 310. The personal computing device 320 may generate an encrypted key for unlocking the reduced-risk device 310 (and/or the locked elements of the reduced-risk device) based on the verification results.

For example, the encrypted key may be generated based on a public key (of a public-private key pair) stored on the personal computing device 320 (such as a public encryption key associated with the reduced-risk device 310, a public key associated with the adult consumer, and/or other public key, etc.), the UID of the reduced-risk device 310, the personal UID of the adult consumer, and/or the verification result, etc., however the example embodiments are not limited thereto and the encrypted key may also be generated based on other information as well.

According to some example embodiments, the identity verification server 330 may generate the encrypted key for unlocking the reduced-risk device 310 based on the verification result. The identity verification server 330 may generate the encrypted key based on a public key stored on the identity verification server 330 (such as a public key associated with the reduced-risk device 310, a public key associated with the adult consumer, and/or other public key, etc.), the UID of the reduced-risk device 310, the personal UID of the adult consumer, and/or the verification result, etc., however the example embodiments are not limited thereto, and the encrypted key may also be generated based on other information as well. For example, the public key may be the UID of the reduced-risk device 310, etc. The identity verification server 330 may then transmit the encrypted key to the personal computing device 320.

Once the personal computing device 320 generates and/or receives the encrypted key, the personal computing device 320 may transmit the encrypted key to the reduced-risk device 310. The reduced-risk device 310 may decrypt the encrypted key using a private key corresponding to the public key used to encrypt the encrypted key. For example, the private key may be a key stored on the reduced-risk device 310 that corresponds to the UID of the reduced-risk device 310, etc. The reduced-risk device 310 may then determine whether the adult consumer was properly verified and/or is legally permitted to operate the locked reduced-risk device 310 and/or the locked elements of the reduced-risk device, based on the verification results included in the encrypted key. If the verification results indicate the adult consumer is properly verified, the reduced-risk device 310 may unlock the reduced-risk device 310 and/or the locked element(s) of the reduced-risk device 310 (e.g., enable the operation of the reduced-risk device 310, the dispersion generating article, the power supply, etc., of the reduced-risk device, etc.). The locked reduced-risk device 310 and/or the locked element(s) of the reduced-risk device may be unlocked for an indeterminate period of time (e.g., permanently unlocked), may be unlocked for a desired period of time (e.g., temporarily unlocked for 15 minutes, 30 minutes, etc.), and/or may be unlocked while a desired unlock condition is satisfied.

For example, the unlocked state of the reduced-risk device 310 may further be conditioned based on whether the reduced-risk device 310 is within a desired distance range of the personal computing device 320. The reduced-risk device 310 may determine whether the reduced-risk device 310 is within a desired distance range of the personal computing device 320 based on a wireless connection established with the personal computing device 320 and/or wireless messages transmitted between the reduced-risk device 310 and the personal computing device 320, and if the wireless connection and/or the wireless messages are disconnected, discontinued, stopped, etc., the reduced-risk device 310 may re-lock itself (e.g., block operation of the reduced-risk device) and/or the previously unlocked element(s) of the reduced-risk device. As another example, the reduced-risk device 310 and/or element(s) of the reduced-risk device may stay unlocked until a condition related to the reduced-risk device itself expires, such as until the dispersion generating article (e.g., cartridge, capsule, heat-stick, etc.) installed on the reduced-risk device is empty and/or replaced, the expiration of a full power supply charge of the reduced-risk device, etc., however the example embodiments are not limited thereto.

According to some example embodiments, the reduced-risk device 310 may also be unlocked using a POS terminal 350 (e.g., kiosk, etc.) installed at the location (e.g., store, etc.) where the reduced-risk device 310 and/or element(s) of the reduced-risk device were purchased. For example, the POS terminal 350 may be a cash register, a computer, a tablet, a computing terminal, and/or a dedicated stand-alone kiosk machine, etc., configured to allow an adult consumer to undergo the identity verification process with the identity verification server 330, and unlock the reduced-risk device 310, without the use of a personal computing device 320. For example, the adult consumer may input their personal information into the POS terminal 350 (e.g., input into a touch screen, a keyboard and mouse, a microphone, a paper scanner, etc.), and once the identity verification server 330 verifies the adult consumer's identity and/or legal ability to buy and operate the reduced-risk device 310, the identity verification server 330 transmits the verification results and/or the encrypted key to the POS terminal 350. The POS terminal 350 may transmit the encrypted key to the reduced-risk device over a wireless and/or wired communication channel, if the reduced-risk device 310 has been removed from its packaging.

Alternatively, the POS terminal 350 may unlock the reduced-risk device 310 by emitting pressurized bursts of air of a desired air pressure and/or frequency to the puff sensor of the reduced-risk device 310, which when received by the reduced-risk device 310, causes the reduced-risk device 310 to unlock. Additionally, the POS terminal 350 may emit a coded sound through a speaker, which is received by a microphone of the reduced-risk device 310, and causes the reduced-risk device 310 to unlock.

Moreover, upon detection of negative air pressure (e.g., a puff) on the mouthpiece of the reduced-risk device 310 by the puff sensor 595, the control circuitry 510 of the reduced-risk device 310 may determine whether the manual lock flag has been set in order to determine whether to enable the operation of the heater 540. If the manual lock flag is set (e.g., the reduced-risk device 310 is in the locked state), the control circuitry 510 does not allow (e.g., prohibits, disables, etc.) the powering of the heater 540 by the power supply 530. If the manual lock flag is not set, the control circuitry 510 allows (e.g., enables, permits, etc.) the powering of the heater 540 by the power supply 530.

Further, the adult consumer may operate software installed on the personal computing device 320, such as reduced-risk device software and/or an app corresponding to the reduced-risk device, etc., which allows the adult consumer to input a manual lock command (e.g., a tap operation, a drag operation, a gesture operation, other touch screen operations, a typed command, etc.) into the graphical user interface (GUI) of the reduced-risk device software. In response to the input of the manual lock command into the GUI of the reduced-risk device software by the adult consumer, the personal computing device 320 transmits a manual lock instruction to the reduced-risk device 310. Once the reduced-risk device 310 receives the manual lock instruction (e.g., disable instruction, etc.) from the personal computing device 320, the reduced-risk device 310 sets the manual lock flag (e.g., lock flag, disable flag, manual disable setting, etc.) in the lock control routine 523 of the memory 520. Upon detection of negative air pressure (e.g., a puff) on the mouthpiece of the reduced-risk device 310 by the puff sensor 595, the control circuitry 510 of the reduced-risk device 310 may determine whether the manual lock flag has been set in order to determine whether to enable the operation of the heater 540. If the manual lock flag is set (e.g., the reduced-risk device 310 is in the locked state), the control circuitry 510 does not allow (e.g., prohibits, disables, etc.) the powering of the heater 540 by the power supply 530. If the manual lock flag is not set, the control circuitry 510 allows (e.g., enables, permits, etc.) the powering of the heater 540 by the power supply 530.

Additionally, the manual lock instruction transmitted by the personal computing device 320 may also include a UID corresponding to the personal computing device 320, such as a unique serial number associated with the personal computing device 320 and/or the reduced-risk device software installed on the personal computing device 320, an IP address and/or MAC address associated with the personal computing device 320, a UID associated with the adult consumer, a UID associated with the reduced-risk device software installed on the personal computing device, etc., and/or a connection session ID corresponding to the communication session established between the personal computing device 320 and the reduced-risk device 310, etc., that may be stored in the lock control routine 523. The UID corresponding to the personal computing device 320 may be used to determine whether the manual lock should be toggled off (e.g., the locked state of the reduced-risk device changed to the unlocked state) based on the reception of a second manual lock instruction (and/or a manual unlock instruction, etc.) from the personal computing device 320. For example, as a security feature, the personal computing device UID included in the first manual lock instruction (e.g., the lock instruction) may be compared with the personal computing device UID included in the second manual lock instruction (e.g., the unlock instruction) to determine whether the personal computing device UIDs match for the first and second manual lock instructions before unlocking the reduced-risk device 310 based on the second manual lock instruction (e.g., the unlock instruction). By verifying that the personal computing device UIDs of the first and second manual lock instructions match before unlocking a previously manually locked reduced-risk device, the security of the reduced-risk device may be increased by decreasing and/or preventing the ability of a person who is not the adult consumer from using a second personal computing device to unlock the manually locked reduced-risk device.

Moreover, the reduced-risk device 310 may include a "proximity lock" feature (e.g., personal computing device proximity lock feature), wherein a reduced-risk device 310 that is in the unlocked state may automatically be placed in the locked state in response to the reduced-risk device 310 becoming disconnected from a paired personal computing device 320. For example, if the adult consumer enables the proximity lock setting (e.g., inputs the proximity lock command on the GUI of the reduced-risk device software) on the reduced-risk device software installed on a personal computing device 320, and the personal computing device 320 is paired with the reduced-risk device 310 over a wireless and/or wired connection, such as a Bluetooth connection, a Near Field Communication (NFC) connection, a WiFi connection, a USB connection, etc., the reduced-risk device software transmits a proximity lock command (e.g., instruction, message, flag, configuration file, etc.) to the reduced-risk device 310 to transition into a proximity lock state. The proximity lock instruction may include a UID corresponding to the personal computing device 320, such as a unique serial number associated with the personal computing device 320 and/or the reduced-risk device software installed on the personal computing device 320, an IP address and/or MAC address associated with the personal computing device 320, a UID associated with the adult consumer, a UID associated with the reduced-risk device software installed on the personal computing device, a connection session ID corresponding to the communication session established between the personal computing device 320 and the reduced-risk device 310, etc. When the reduced-risk device 310 receives the proximity lock instruction, the reduced-risk device 310 is put into a "proximity lock" state (e.g., a proximity lock flag is set in the lock control routine 523 of the memory 520), wherein the reduced-risk device 310 may only be operated by the adult consumer if the reduced-risk device 310 connection to the personal computing device 320 is maintained.

Accordingly, similar to the manual lock setting, upon detection of negative air pressure (e.g., a puff) on the mouthpiece of the reduced-risk device 310 by the puff sensor 595, the control circuitry 510 of the reduced-risk device 310 may determine whether the proximity lock flag has been set in order to determine whether to enable the operation of the heater 540 in response to the detected negative air pressure. If the proximity lock flag is set (e.g., the reduced-risk device 310 is in the locked state), the control circuitry 510 determines whether the reduced-risk device 310 is connected to the same personal computing device that set the proximity lock (e.g., the personal computing device 320 that transmitted the initial proximity lock instruction, etc.) based on the personal computing device UIDs included in the initial proximity lock instruction and the subsequent proximity lock instruction. In response to the personal computing device UIDs not matching, the control circuitry 510 does not allow (e.g., prohibits, disables, etc.) the powering of the heater 540 by the power supply 530. In response to the personal computing device UIDs matching, the control circuitry 510 allows (e.g., enables, permits, etc.) the powering of the heater 540 by the power supply 530.

According to some example embodiments, the identity verification system may also include a "beacon proximity lock" feature, wherein a reduced-risk device 310 that is in the unlocked state may automatically be placed in the locked state in response to the reduced-risk device 310 receiving a wireless lock signal from a wireless beacon transmitter 360. The wireless beacon transmitter 360 may be a Bluetooth beacon transmitter, a WiFi beacon transmitter, an NFC transmitter, etc., but the example embodiments are not limited thereto. The wireless beacon transmitter 360 may be installed in a location and/or vehicle, etc., that prohibits and/or restricts the operation of reduced-risk device, such as a school, place of worship, a youth facility, a government facility, a designated non-smoking area, an airport, an airplane, a train, a mass transit vehicle, etc., and may transmit the wireless lock signal to reduced-risk devices within the vicinity of the restricted location. When the reduced-risk device 310 receives the wireless lock signal, the control circuitry 510 of the reduced-risk device 310 places the reduced-risk device 310 into a "beacon proximity lock" state (e.g., a beacon proximity lock flag is set in the lock control routine 523 of the memory 520), wherein the reduced-risk device 310 does not permit the operation of the reduced-risk device 310 until the reduced-risk device 310 is out of range of the wireless beacon transmitter 360 (e.g., the reduced-risk device 310 does not receive the wireless lock signal from the wireless beacon transmitter 360). The wireless beacon transmitter 360 may transmit the wireless lock signal periodically, with the wireless lock signal including information indicating the amount of time that the reduced-risk device 310 should remain in the locked state prior to the reduced-risk device 310 determining whether an additional wireless lock signal has been received from the wireless beacon transmitter 360. In other words, if the reduced-risk device 310 receives a wireless lock signal from the wireless beacon transmitter 360, the reduced-risk device 310 may extract a lockdown period from the wireless lock signal (e.g., 30 seconds, 5 minutes, 15 minutes, etc.), and start a countdown from the time that the wireless lock signal was received before the adult consumer may attempt to unlock the reduced-risk device 310. If another wireless lock signal is received by the reduced-risk device 310 before the lockdown period expires, the lockdown period resets and the countdown begins again.

Additionally, in accordance with at least one example embodiment, the identity verification service may evaluate an identity verification request to determine whether the identity verification request is suspicious and/or possibly fraudulent based on the location information included with the identity verification request and information stored in the adult consumer's profile. For example, the previously stored location information of the reduced-risk device 310 and/or the personal computing device 320 may be included with the identity verification request in order to identify the location of suspicious identity verification activity and/or prohibited reduced-risk device operation based on the geographic location. Referring again to the identity verification method, the location information of the reduced-risk device 310 and/or the personal computing device 320 may be associated with each identity verification request and may be transmitted to the identity verification server 330 to determine the location of the adult consumer at the time of the identity verification request. In the event that suspicious identity verification activity is detected, such as one or more consecutive identity verification attempt failures, the total number of identity verification failures exceeding a desired threshold number for a desired time period, identity verification attempts that are determined to be out of character for the adult consumer based on the temporal and/or spatial characteristics of the identity verification attempts (e.g., the identity verification attempt occurs in a geographical location that is not associated with the adult consumer, the identity verification attempt that occurs at a time that is out of character for the adult consumer, the identity verification attempt occurs in a geographical location that has been previously identified as a location associated with a higher probability of suspicious, prohibited, and/or false identity verification attempts, such as a location where only minors are likely to be located (e.g., a school, etc.), or a retail location suspected of illegally selling reduced-risk devices to minors, etc.), the identity verification attempt occurs using a personal computing device that is not associated with the adult consumer (e.g., a previously un-registered personal computing device), etc. Each identity verification request may be analyzed for suspicious activity by comparing the characteristics (e.g., time, date, location, success/failure of the request, etc., information) of the identity verification request with the data stored on the identity verification server 330 associated with the adult consumer's previous identity verification requests (e.g., historical identity verification data) to determine whether the identity verification request should be determined to be suspicious and/or flagged as suspicious. Additionally, characteristics of each identity verification request may be compared to general identity verification data, such as locations of known and/or suspected stores selling reduced-risk devices to minors, known locations of schools, youth facilities, known locations where reduced-risk device activity is prohibited, etc., to determine whether the identity verification request should be determined to be suspicious and/or flagged as suspicious. However, the example embodiments are not limited thereto, and other characteristics may be analyzed to detect suspicious identity verification activity.

In the event that an identity verification request is determined to be suspicious, a suspicious identity verification activity notification may be transmitted to a known point of contact previously registered by the adult consumer with the identity verification service, such as a telephone number, email address, mailing address, social networking service (SNS) account, an instant messaging service account, the reduced-risk device software installed on the personal computing device 320 associated with the adult consumer, etc., for the adult consumer corresponding to the identity verification request regarding the suspicious identity verification request (e.g., the identity input into the identity verification request). For example, the contact information for the adult consumer may be stored in the profile information associated with the adult consumer in the verification information database 623 of the identity verification server 330, etc. The suspicious identity verification notification may include details regarding the identity verification request, such as the name of the adult consumer input into the identity verification request, and/or the date, the time, the location, etc., of the request, etc.

The suspicious identity verification notification may also include a request for the adult consumer to confirm that the adult consumer initiated the suspicious identity verification request. For example, the suspicious identity verification notification may include a URL link for the adult consumer to engage in order to confirm/deny the suspicious identity verification request, may include a telephone number for the adult consumer to call and/or send a reply SMS message to verify the suspicious identity verification request, may include an instant messaging account to send a response to regarding the suspicious identity verification request, and/or the adult consumer use a messaging function of the reduced-risk device software to respond to the suspicious identity verification request, etc., however the example embodiments are not limited thereto.

When the adult consumer responds to the suspicious identity verification notification and indicates that the adult consumer initiated the identity verification request (e.g., the identity verification request is not fraudulent, etc.), then the identity verification server 330 may change the designation of the corresponding identity verification request as being not being suspicious in the verification information database 623, and the identity verification server 330 may transmit the results of the identity verification to the reduced-risk device 310 as discussed above. If the adult consumer responds to the suspicious identity verification notification and confirms that the suspicious identity verification request was fraudulent (and/or the adult consumer fails to respond to the suspicious identity verification notification within a desired time period), the identity verification server 330 transmits the results of the identity verification request to the personal computing device 320, the results indicating the identity verification request was confirmed to be suspicious and/or fraudulent, and the personal computing device 320 treats the confirmed suspicious and/or fraudulent result to be the equivalent of a failed identity verification attempt. Further, the identity verification server 330 may also include permanent lock instructions in the results of the identity verification based on the number of failed and/or confirmed suspicious identity verification requests received from the adult consumer and/or the personal computing device 320, the reduced-risk device software of the personal computing device 320 causes the reduced-risk device 310 and/or the elements of the reduced-risk device to be placed in a permanent lock state (e.g., permanent age/identity lock state), wherein the reduced-risk device 310 and/or the elements of the reduced-risk device 310 may not be unlocked using the identity verification system.

Moreover, if identity verification server 330 determines that the number of failed and/or confirmed suspicious identity verification requests reaches a desired threshold number, a notification may also be transmitted to legal authorities with the relevant information regarding the failed and/or confirmed suspicious identity verification requests, such as information related to the adult consumer identity that was used for the identity verification requests, the locations of the identity verification requests, the date/time of the identity verification requests, etc., to enable the legal authorities associated with the location of the failed and/or confirmed suspicious identity verification requests to investigate the failed and/or confirmed suspicious identity verification requests, such as investigating a retail store to determine whether the retail store is illegally selling reduced-risk devices to minors, etc. Additionally, if the adult consumer indicates that a particular suspicious identity verification request was suspicious and/or fraudulent, the adult consumer may select an option in the GUI of the reduced-risk device software to forward the relevant information regarding the confirmed suspicious identity verification request to the legal authorities as well.

Figure 4A:
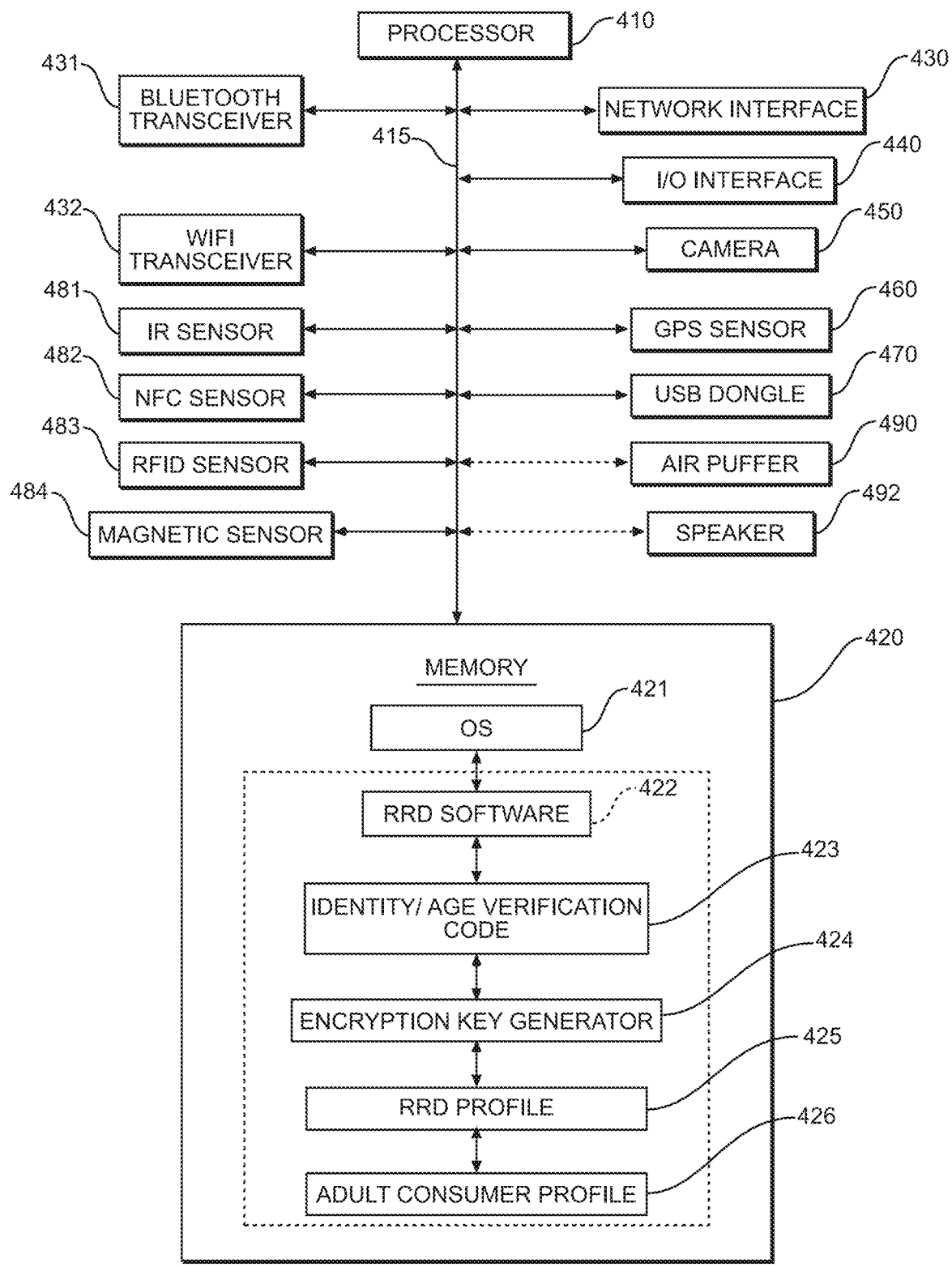
FIG. 4A is a block diagram illustrating various elements of a personal computing device for the identity verification system according to at least one example embodiment.

FIG. 4A is a block diagram illustrating various elements of a personal computing device for the identity verification system according to at least one example embodiment.

According to at least one example embodiment, a personal computing device, such as the personal computing device 320 of FIG. 3, may include at least one processor 410, a communication bus 415, and/or a memory 420, etc. The memory 420 may include computer readable instructions (and/or software code, etc.) corresponding to an operating system (OS) 421 for operating the personal computing device, and special purpose computer readable instructions related to the locking/unlocking of the reduced-risk device and/or the identity verification process, such as reduced-risk device (RRD) software 422, an identity/age verification routine 423, an encryption key generator 424, a reduced-risk device (RRD) profile 425, and/or an adult consumer profile 426, etc. However, the example embodiments are not limited thereto, and according to some example embodiments, one or more of the operating system (OS) 421, the reduced-risk device (RRD) software 422, the identity/age verification routine 423, the encryption key generator 424, the reduced-risk device (RRD) profile 425, and/or the adult consumer profile 426 may be combined into one or more routines, for example, the RRD software 422 may include the identity/age verification routine 423, encryption key generator 424, the reduced-risk device (RRD) profile 425, and/or the adult consumer profile 426, etc.

In at least one example embodiment, the processor 410 may be at least one processor (and/or processor cores, distributed processors, networked processors, etc.), which may be configured to control one or more elements of the personal computing device 320. The processor 410 is configured to execute processes by retrieving program code (e.g., computer readable instructions) and data from the memory 420 to process them, thereby executing control and functions of the personal computing device 320. Once the program instructions are loaded into the processor 410, the processor 410 executes the program instructions, thereby transforming the processor 410 into a special purpose processor. For example, once the processor 410 loads the special purpose instructions related to the reduced-risk device (RRD) software 422, the identity/age verification routine 423, the encryption key generator 424, the RRD profile 425, and/or the adult consumer profile 426, the processor 410 is transformed into a special purpose processor for executing the routines of the RRD software 422, the identity/age verification routine 423, the encryption key generator 424, the reduced-risk device RRD profile 425, and/or the adult consumer profile 426, etc.

In at least one example embodiment, the memory 420 may be a non-transitory computer-readable storage medium and may include a random access memory (RAM), a read only memory (ROM), and/or a permanent mass storage device such as a disk drive, a solid state drive, etc. Stored in the memory 420 are computer readable instructions (e.g., program code) for the reduced-risk device (RRD) software 422, the identity/age verification routine 423, the encryption key generator 424, the reduced-risk device (RRD) profile 425, and/or the adult consumer profile 426, etc. Additionally, the memory 420 may store additional data (not shown) for use with the stored program code, such as sensor information, program setting data, reduced-risk device data, etc. Such software elements may be loaded from a non-transitory computer-readable storage medium independent of the memory 420, using a drive mechanism (not shown) connected to the personal computing device 320 through a network interface 430. The network interface 430 may include a wired communication interface for a wired communication protocol, such as Ethernet, USB, FireWire, eSATA, ExpressCard, Thunderbolt, etc., and/or may include a wireless communication interface for a wireless communication protocol, such as WiFi, Bluetooth, Near Field Communication (NFC), 3G, 4G LTE, 5G, Zigbee, etc. For example, the network interface may include a Bluetooth transceiver 431, a WiFi transceiver 432, an IR sensor 481, NFC sensor 482, a RFID sensor 483, a magnetic sensor 484, etc.

Additionally, the network interface 430 may enable the processor 410 to communicate with and/or transfer data to/from the reduced-risk device 310, the identity verification server 330, the third party identity verification service 340, the POS terminal 350, and/or other computing devices (not shown), such as a server, a personal computer (PC), a laptop, a smartphone, a tablet, a gaming device, etc. Examples of data transferred between the processor 410 and the reduced-risk device 310 may include the identity verification results, the encrypted key, profile data related to one or more adult consumers, software updates to the reduced-risk device (RRD) software 422, the identity/age verification routine 423, the encryption key generator 424, the reduced-risk device (RRD) profile 425, and/or the adult consumer profile 426, etc.

In at least one example embodiment, the communication bus 415 may enable communication and data transmission to be performed between elements of the personal computing device 320. The bus 415 may be implemented using a high-speed serial bus, a parallel bus, and/or any other appropriate communication technology.

The personal computing device 320 may also include at least one input/output (I/O) interface 440 for connecting to one or more I/O devices, such as a keyboard (not shown), mouse (not shown), microphone (not shown), speaker (not shown), sensors (e.g., gyroscopes (not shown), accelerometers (not shown), GPS sensor 460, other position and location sensors (not shown), pressure sensors (not shown), etc.), a camera 450, etc. The I/O devices may be integrated into the personal computing device 320, external to the personal computing device 320 and connected to the personal computing device 320 via a wired and/or wireless connection, etc. Additionally, the personal computing device 320 may also include at least one display (not shown), such as a monitor, a TV, a touchscreen panel, and/or a projector, etc.

Further, according to some example embodiments, a USB dongle 470 may be connected to the personal computing device 320, such as a personal computer (PC), a laptop, a tablet, etc. The USB dongle 470 may be a "plug-in" type device that enables personal computing devices that includes one or more of the Bluetooth transceiver 431, WiFi transceiver 432, IR sensor 481, NFC sensor 482, RFID sensor 483, magnetic sensor 484, etc., to allow the personal computing device to communicate with the reduced-risk device 310, particularly if the personal computing device does not already include one or more of these sensors.

Additionally, according to some example embodiments, the personal computing device 320 may be a POS terminal and/or a special purpose device located at a retail location, store, place of purchase, etc., to enable an adult consumer and/or retail employee, vendor, etc., to unlock the reduced-risk device 310 after purchase. According to these example embodiments, the personal computing device 320 may include an air puffing mechanism 490 and/or speaker 492 to emit a specialized code to unlock the reduced-risk device 310 after the adult consumer has verified his or her age and/or identity via the special purpose personal computing device 320 located at the retail location. After the adult consumer undergoes the age and/or identity verification process using the personal computing device 320, the personal computing device 320 receives the results of the verification and/or the encrypted key from the identity verification server 330. If the personal computing device 320 receives the verification results from the identity verification server 330, then the personal computing device 320 generates an encrypted key based on the verification results. The personal computing device 320 also specially encodes the encrypted key using the air puffing mechanism 490 and/or the speaker 492 to transmit the encrypted key to the reduced-risk device 310. For example, if the personal computing device 320 uses the air puffing mechanism 490, the encrypted key will be converted (e.g., translated, transformed, etc.) into special air puff "patterns" to be generated by the air puffing mechanism 490, which when detected by the puff sensor of the reduced-risk device 310, will be translated into data by the reduced-risk device 310, etc. If the personal computing device 320 uses the speaker 492 to transmit the encrypted key to the reduced-risk device 310, the encrypted key is converted into encoded sound waves that are detected by the microphone of the reduced-risk device 310, and the reduced-risk device 310 translates the encoded sounds into data, etc.

Figure 4B:
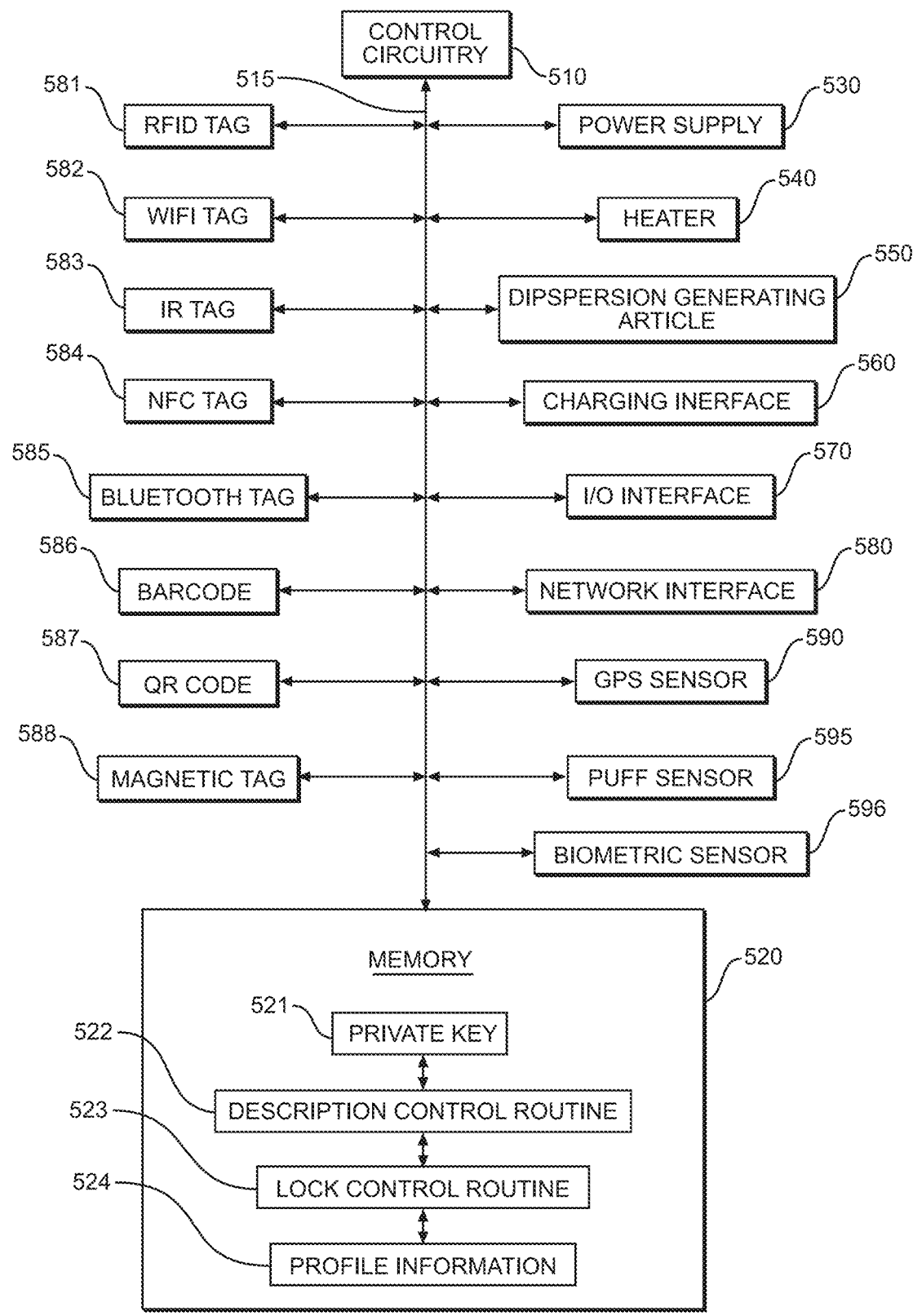
FIG. 4B is a block diagram illustrating various elements of a reduced-risk device for the identity verification system according to at least one example embodiment.

FIG. 4B is a block diagram illustrating various elements of a reduced-risk device for the identity verification system according to at least one example embodiment.

According to at least one example embodiment, a reduced-risk device, such as the reduced-risk device 310, etc., may include control circuitry 510, a memory 520, a bus 515, a power supply 530, a heater 540, a dispersion generating article 550, a charging interface for the power supply 560, an input/output (I/O) interface 570, a network interface 580, a GPS sensor 590, a puff sensor 595, and/or a biometric sensor 596, etc. However the example embodiments are not limited thereto, and the reduced-risk device may include a greater or lesser number of constituent elements.

Additionally, the reduced-risk device may also include one or more reduced-risk device UID tags, such as a RFID tag 581, a WiFi tag 582, an infra-red (IR) tag 583, a NFC tag 584, a Bluetooth tag 585, a barcode 586, a QR code 587, a magnetic tag 588, etc. According to at least one example embodiment, the reduced-risk device UID tags may include (e.g., store, have programmed, have embedded, and/or have information printed on them, etc.) unique identifying information (e.g., UID, etc.) corresponding to the reduced-risk device itself, and/or to individual elements of the reduced-risk device, such as the power supply 530, the heater 540, the dispersion generating article 550, the charging interface 560, the I/O interface 570, the network interface 580, the GPS sensor 590, and/or the puff sensor 595, etc. The UID information included in the reduced-risk device UID tags may be read by a corresponding reader and/or sensor of a personal computing device and/or POS terminal, such as the personal computing device 320, the POS terminal 350, respectively, etc., and/or a stand-alone reader and/or sensor. For example, if the reduced-risk device UID tag is a RFID tag 581, the UID information may be read using a corresponding RFID scanner, etc. If the reduced-risk device UID tag is a barcode 586 or QR code 587, the UID information may be read using a camera, barcode scanner, etc. Additionally, the reduced-risk device UID tag may also be serial number that is printed or etched on the reduced-risk device, that may be read by an adult consumer and/or store employee, etc., and input into the personal computing device 320 or POS terminal 350, etc. According to at least one example embodiment, the reduced-risk device UID tags may be located on the reduced-risk device 310, elements of the reduced-risk device 310 (e.g., the dispersion generating article 550, the power supply 530, etc.), and/or located on the packaging for the reduced-risk device 310 or the elements of the reduced-risk device, etc.

In at least one example embodiment, the memory 520 may be a non-transitory computer-readable storage medium and may include a random access memory (RAM), a read only memory (ROM), and/or a permanent mass storage device such as a solid state drive, etc. Stored in the memory 520 is program code (i.e., computer readable instructions) for functions of the entire reduced-risk device 310 and/or functions related to the locking/unlocking of the reduced-risk device and/or elements of the reduced-risk device, such as a decryption control routine 522, heater control routine 523, and/or profile information 524 (e.g., reduced-risk device profile information, dispersion generating article profile information, adult consumer profile information, etc.), as well as data, such as a private key 521, biometric information captured using the biometric sensor 596, etc. Such software elements may be loaded from a non-transitory computer-readable storage medium independent of the memory 520, via a wired communication protocol, such as Ethernet, USB, FireWire, eSATA, ExpressCard, Thunderbolt, etc., and/or wireless communication protocols, such as Wi-Fi, Bluetooth, Near-Field Communications (NFC), Infra-Red (IR) communications, RFID communications, 3G, 4G LTE, 5G, etc. Additionally, some or all of the functions and/or data stored on the memory 520 may be stored in an encrypted state, such as the private key 521, the profile information, etc.

In at least one example embodiment, the bus 515 may enable communication and data transmission to be performed between elements of the reduced-risk device 310. The bus 515 may be implemented using a high-speed serial bus, a parallel bus, and/or any other appropriate communication technology.

According to at least one example embodiment, the control circuitry 510 may be at least one controller, processor, processing device, field programmable gate array (FPGA), system-on-chip (SoC), and/or hardwired circuitry, etc., which may be configured to control one or more elements of the reduced-risk device 310. The control circuitry 510 may also retrieve program code (e.g., computer readable instructions), such as the decryption control routine 522, the heater control routine 523, and/or the profile information 524 (e.g., reduced-risk device profile information, dispersion generating article profile information, etc.), etc., and data from the memory 520 (e.g., a private key 521, etc.) to process them, thereby executing control and functions of the entire reduced-risk device 310 and/or functions related to the locking/unlocking of the reduced-risk device and/or elements of the reduced-risk device. Once the program code are loaded into the control circuitry 510, the control circuitry 510 executes the special purpose program instructions, thereby transforming the control circuitry 510 into a special purpose controller and/or processor, etc. Additionally, according to some example embodiments, the control circuitry 510 may be two or more controllers, processor, processing device, field programmable gate array (FPGA), system-on-chip (SoC), and/or hardwired circuitry, etc., with a first controller dedicated to executing the control and functions of the reduced-risk device, and a second controller dedicated to the functions related to the locking/unlocking of the reduced-risk device and/or elements of the reduced-risk device, etc.

In at least one example embodiment, the control circuitry 510 may control the network interface 580 to receive an encrypted key from the personal computing device 320, the POS terminal 350, etc. The control circuitry 510 may decrypt the received encrypted key using the decryption control routine 522 and the private key 521, and based on the identity verification result and the reduced-risk device UID (and/or reduced-risk device element UID) included in the encrypted key, determine whether to unlock the reduced-risk device 310 and/or unlock the corresponding element of the reduced-risk device, such as the dispersion generating article 550, the power supply 530, the heater 540, the charging interface 560, etc. Additionally, according to some example embodiments, the control circuitry 510 may control the biometric sensor 596 to capture biometric information (e.g., a fingerprint scan, a retina scan, a voice scan, a face scan, a heartbeat scan, etc.) of an adult consumer and may transmit the biometric information to the personal computing device 320 for verifying the identity of the adult consumer, etc.

According to at least one example embodiment, the puff sensor 595 may receive pressurized bursts of air from a POS terminal 350 and/or an air puffing device (e.g., air puff generator, etc.) located at a retail store, etc. If the received pressurized bursts of air are of a desired air pressure and/or frequency, the control circuitry 510 may determine to unlock the reduced-risk device 310 and/or elements of the reduced-risk device. Additionally, the reduced-risk device 310 may receive a coded sound emitted through a speaker of the POS terminal 350, etc., which is received by a microphone (not shown) of the reduced-risk device 310. If the received coded sound matches a desired coded sound, the control circuitry 510 may determine to unlock the reduced-risk device 310 and/or unlock elements of the reduced-risk device. The pressurized bursts of air and/or the coded sounds may be encoded using a desired air pressure-based or sound-based data format known to the control circuitry 510, such that the bursts of air and the sounds may be translated into digital data by the control circuitry 510. The translated digital data may correspond to the identity verification results and the UID of the reduced-risk device 310 and/or elements of the reduced-risk device that the adult consumer is attempting to unlock.

In at least one example embodiment, the control circuitry 510 may execute the lock control routine 523 to unlock the reduced-risk device 310 and/or the individual elements of the reduced-risk device 310 based on the results of the determination of whether to unlock the reduced-risk device 310. When the control circuitry 510 determines that the reduced-risk device 310 is to be unlocked, the control circuitry 510 may enable the power supply 530 to transmit power to the heater 540 of the reduced-risk device 310. Additionally, when the control circuitry 510 determines that an individual element and/or elements of the reduced-risk device 310 is to be unlocked, the control circuitry 510 may enable the operation of those elements by manipulating electrical and/or physical switches connected to those elements, such as the dispersion generating article 550, the puff sensor 595, etc. The reduced-risk device 310 and/or the elements of the reduced-risk device 310 may be permanently unlocked or temporarily unlocked based on the settings of the reduced-risk device 310 and/or lock condition settings included in the encrypted key.

Moreover, the control circuitry 510 may also execute the lock control routine 523 to lock the reduced-risk device 310 and/or the individual elements of the reduced-risk device 310 based on at least one lock/unlock condition, such as an unlock period expiring, the proximity of the reduced-risk device 310 to the personal computing device 320, the proximity of the reduced-risk device 310 to a location that the operation of the reduced-risk device 310 is prohibited, receiving of a lock signal, etc. For example, the control circuitry 510 may re-lock the reduced-risk device 310 and/or the individual elements of the reduced-risk device after the expiration of a set time period included in the lock condition settings of the encrypted key and/or programmed into the reduced-risk device 310. Additionally, the control circuitry 510 may re-lock the reduced-risk device 310 when the reduced-risk device 310 is out of a desired proximity range (e.g., a desired distance range) from the personal computing device 320. The desired proximity range may be based on a connection range of the wireless protocol, such as Bluetooth, NFC, WiFi, etc., used to wirelessly connect the network interface 580 of the reduced-risk device 310 with the network interface 430 of the personal computing device 320, etc.

The control circuitry 510 may also re-lock the reduced-risk device 310 based on location information corresponding to the current location of the reduced-risk device 310. For example, the reduced-risk device 310 may include a location sensor, such as a GPS sensor 590, a GLONASS sensor (not shown), etc., that determines the current location information of the reduced-risk device 310, or the current location information may be determined based on location information of the personal computing device 320 when it is connected to the reduced-risk device 310. The control circuitry 510 may compare the location information associated with the reduced-risk device 310 with location information of places where the operation of the reduced-risk device 310 may be prohibited and/or restricted, such as educational facilities, places of worship, public venues, medical facilities, etc., or places input by the adult consumer, such as the location information corresponding to the adult consumer's home, office, etc. The location information of restricted location may be stored in the memory 520 of the reduced-risk device 310 and/or may be transmitted to the reduced-risk device 310 from the personal computing device 320, etc., but is not limited thereto.

The control circuitry 510 may also re-lock the reduced-risk device 310 based on the reception of a wireless lock signal emitted from a wireless beacon transmitter 360, such as a Bluetooth beacon transmitter, a WiFi beacon transmitter, etc. The wireless beacon transmitter 360 may be installed in a location that prohibits and/or restricts the operation of reduced-risk device, such as a school, place of worship, etc., and may transmit the wireless lock signal to reduced-risk devices within the vicinity of the restricted location. When the control circuitry 510 detects that the network interface 580 has received the wireless lock signal from the wireless beacon transmitter 360, the control circuitry 510 may disable the power supply from transmitting power to the heater 540, etc.

While FIG. 4B depicts an example embodiment of a reduced-risk device, the reduced-risk device is not limited thereto, and may include additional and/or alternative architectures that may be suitable for the purposes demonstrated. For example, the reduced-risk device may include a plurality of additional or alternative elements, such as additional processing devices, interfaces, and memories.

Figure 4C:
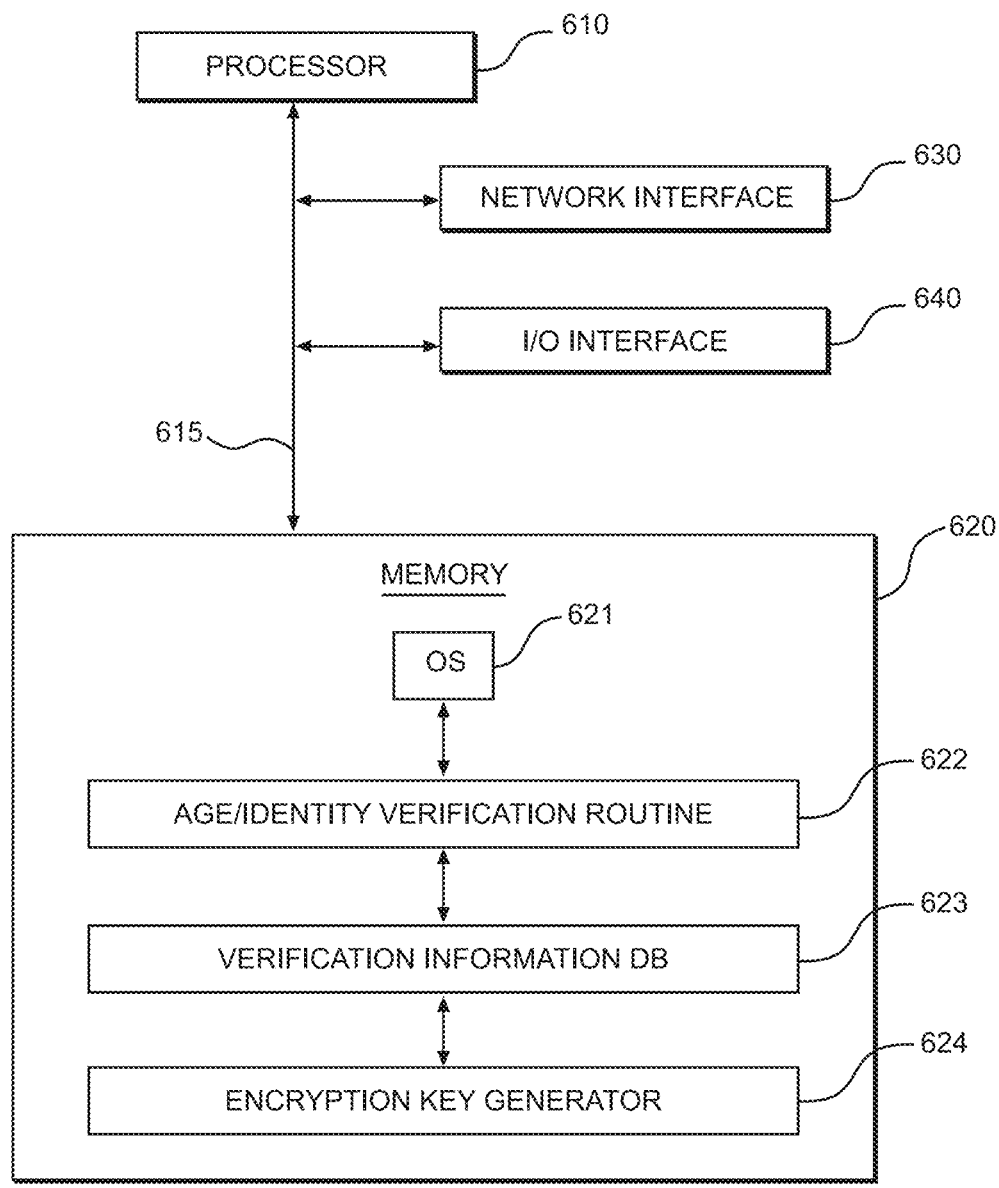
FIG. 4C is a block diagram illustrating various elements of identity verification server for the identity verification system according to at least one example embodiment.

FIG. 4C is a block diagram illustrating elements of an identity verification server according to at least one example embodiment. Description of elements in the identity verification server which are the same as elements described in connection with FIG. 4A will be partially or completely omitted and the same elements may be assumed to have the same and/or similar characteristics and/or operation as the elements described in connection with FIG. 4A. Differences between the personal computing device and the identity verification server will be described below.

According to at least one example embodiment, an identity verification server, such as the identity verification server 330 of FIG. 3, may include at least one processor 610, a communication bus 615, a memory 620, a network interface 630, and/or an I/O interface 640, etc. The memory 620 may include computer readable instructions (and/or software code, etc.) corresponding to an operating system (OS) 621 for operating the identity verification server, and special purpose computer readable instructions related to the identity verification process, such as an age/identity verification routine 622, a verification information database 623 for storing age and/or identity verification information related to a plurality of adult consumers, an encryption key generator 624, etc., but the example embodiments are not limited thereto.

In at least one example embodiment, the processor 610 may be at least one processor (and/or processor cores, distributed processors, networked processors, etc.), which may be configured to control one or more elements of the identity verification server 330. The processor 610 is configured to execute processes by retrieving program code (e.g., computer readable instructions) and data from the memory 620 to process them, thereby executing control and functions of the identity verification server 330. Once the program instructions are loaded into the processor 610, the processor 610 executes the program instructions, thereby transforming the processor 610 into a special purpose processor. For example, once the processor 610 loads the special purpose instructions related to the age/identity verification routine 622, the verification information database 623, the encryption key generator 624, etc., the processor 610 is transformed into a special purpose processor for executing the routines of the age/identity verification routine 622, the verification information database 623, the encryption key generator 624, etc.

Additionally, according to at least one example embodiment, the processor 610 may execute the age/identity verification routine 622 to perform an age and/or identity verification of an adult consumer based on information received from the personal computing device 320 and/or the POS terminal 350, etc., using the network interface 630. The information received from the personal computing device 320 and/or the POS terminal 350 may include a request for age and/or identity verification, the UID of the reduced-risk device and/or UID of elements of the reduced-risk device, as well as information related to the identity of the adult consumer requesting age/identity verification (e.g., the personal UID corresponding to the adult consumer, the name of the adult consumer, etc.). The processor 610 may then generate age and/or identity verification challenge questions based on the received identity information of the adult consumer and verified identification information stored in the verification information database 623 corresponding to the received age/identity verification request, such as questions regarding personal information of the adult consumer, questions regarding family members of the adult consumer, public financial information regarding the adult consumer, business information regarding the adult consumer, biometric information of the adult consumer, etc., stored in the verification information database 623 and have been previously verified as being accurate information related to the adult consumer. The identity verification challenge questions may be questions that the adult consumer has previously created and/or submitted answers for, or may be questions and answers collected by a third party and/or external identity verification service 340 based on information available regarding the adult consumer, such as public records, financial data, information provided by the adult consumer to the identity verification server 330, information provided to the identity verification software application, biometric data of the adult consumer, etc. Once the processor 610 generates the age and/or identity verification challenge questions, the processor 610 may transmit the challenge questions to the personal computing device 320 and/or the POS terminal 350 using the network interface 630.

Alternatively, according to at least one example embodiment, the processor 610 may contact a third party server, such as the third party identity verification service 340, a third party credit report/information service, a government database, etc., to generate the verification challenge questions for the adult consumer based on information corresponding to the adult consumer stored on the third party server. Once the processor 610 receives the verification challenge questions from the third party server, the processor 610 may transmit the verification challenge questions to the personal computing device 320 and/or POS terminal 350, etc., using the network interface 630.

The processor 610 may receive response(s) to the identity verification challenge question(s) from the personal computing device 320 and/or the POS terminal 350, etc., using the network interface 630, and the processor 610 may verify the responses based on the identity verification information corresponding to the adult consumer stored in the verification information database 623 of the identity verification server 330. According to some example embodiments, the verification information database 623 may be hosted by a third party server, such as a third party identity verification service, a third party credit report/information service, a government database, etc., which may be accessed in order to verify the information included in the response(s) to the identity verification challenge question(s) received from the personal computing device 320 and/or the POS terminal 350, etc. Additionally, once the identity of the adult consumer requesting the unlocking of the locked reduced-risk device 310 and/or locked element(s) of the reduced-risk device is confirmed, the processor 610 may also determine whether the adult consumer is of legal age (e.g., meets a legal age) to purchase and/or operate the reduced-risk device 310, by checking the stored age of the confirmed identity with the minimum legal age to purchase and/or operate a reduced-risk device and/or elements of the reduced-risk device (e.g., a dispersion generating article 550 for the reduced-risk device), etc., in the appropriate jurisdiction. For example, geographic information related to the location of the reduced-risk device 310, the location of the personal computing device 320, and/or the POS terminal 350 may be transmitted to the identity verification server 330. The geographic information may be determined using a GPS sensor and/or other location determining sensor/device, etc., of the reduced-risk device 310, the personal computing device 320, and/or the POS terminal 350, may be a location associated with the store at which the reduced-risk device 310 is being purchased, may be a pre-defined address associated with the adult consumer's mailing address, etc.

Based on the results of the verification of the responses to the identity verification challenge question(s), the processor 610 generates an encryption key using the encryption key generator 624. The processor 610 may generate the encryption key based on the results of the verification (e.g., indicating that the information included in the response received from the adult consumer was successfully verified using the information stored on the verification information database 623, or that the information included in the response did not match the information stored on the verification information database 623, etc.), the UID of the reduced-risk device 310 and/or UID(s) of the element(s) of the reduced-risk device 310 that the adult consumer requests to unlock, etc. For example, the processor 610 may generate the encryption key based on a public key corresponding to the reduced-risk device 310 and/or the element(s) of the reduced-risk device 310, the UID of the reduced-risk device and/or the element(s) of the reduced-risk device, and the results of the verification, etc., the public key being stored on the identity verification server 330, and transmit the encryption key to the personal computing device 320 and/or the POS terminal 350. However, the example embodiments are not limited thereto, and the encryption key may be generated based on other data.

According to some example embodiments, the UID(s) of the reduced-risk device 310 and/or the element(s) of the reduced-risk device may be the public key itself, but the example embodiments are not limited thereto. Additionally, according to other example embodiments, the processor 610 may omit the generation of the encryption key, and may instead transmit the results of the verification to the personal computing device 320 and/or POS terminal 350, and the personal computing device 320 and/or POS terminal 350 may generate the encryption key in a similar manner. Moreover, according to still other example embodiments, the processor 610 may transmit the generated encryption key or the results of the verification directly to the reduced-risk device 310 itself, etc.

Additionally, according to some example embodiments, the processor 610 may log verification attempts in the verification information database 623. For example, the processor 610 may log all verification attempts, or may log unsuccessful verification attempts, in the verification information database 623. Data included in the verification attempt logs may include the date, time, adult consumer identity used in the verification attempt, result of the verification attempt, UID of the reduced-risk device and/or element of the reduced-risk device corresponding to the verification attempt, IP address and/or MAC address of the personal computing device and/or POS terminal associated with the verification attempt, location information (e.g., GPS information, latitude/longitude, street address associated with the POS terminal, etc.) associated with the personal computing device and/or POS terminal associated with the verification attempt, store/retail employee information associated with the point-of-sale of the reduced-risk device, etc., but the example embodiments are not limited thereto, and other information may also be logged. Further, information related to unsuccessful verification attempts may be forwarded to relevant authorities, such as governmental agencies (e.g., law enforcement, public health officials, state regulators, etc.), school officials, employers, etc., so that possible illegal activity related to the sale or consumption of reduced-risk devices to minors, etc., may be monitored and/or remediated. Additionally, information related to unsuccessful verification attempts may also be forwarded to an address (e.g., mailing address, email address, phone number, etc.) associated with the identity of the adult consumer that the request attempted to verify, etc., so that the authentic adult consumer may be informed of unsuccessful attempts to use the adult consumer's identity to pass an age/identity verification for the unlocking of a reduced-risk device.

While FIG. 4C depicts an example embodiment of an identity verification server, the identity verification server is not limited thereto, and may include additional and/or alternative architectures that may be suitable for the purposes demonstrated. For example, the identity verification server 330 may include a plurality of additional or alternative elements, such as additional processing devices, interfaces, routines, and memories, etc.

Figure 5:
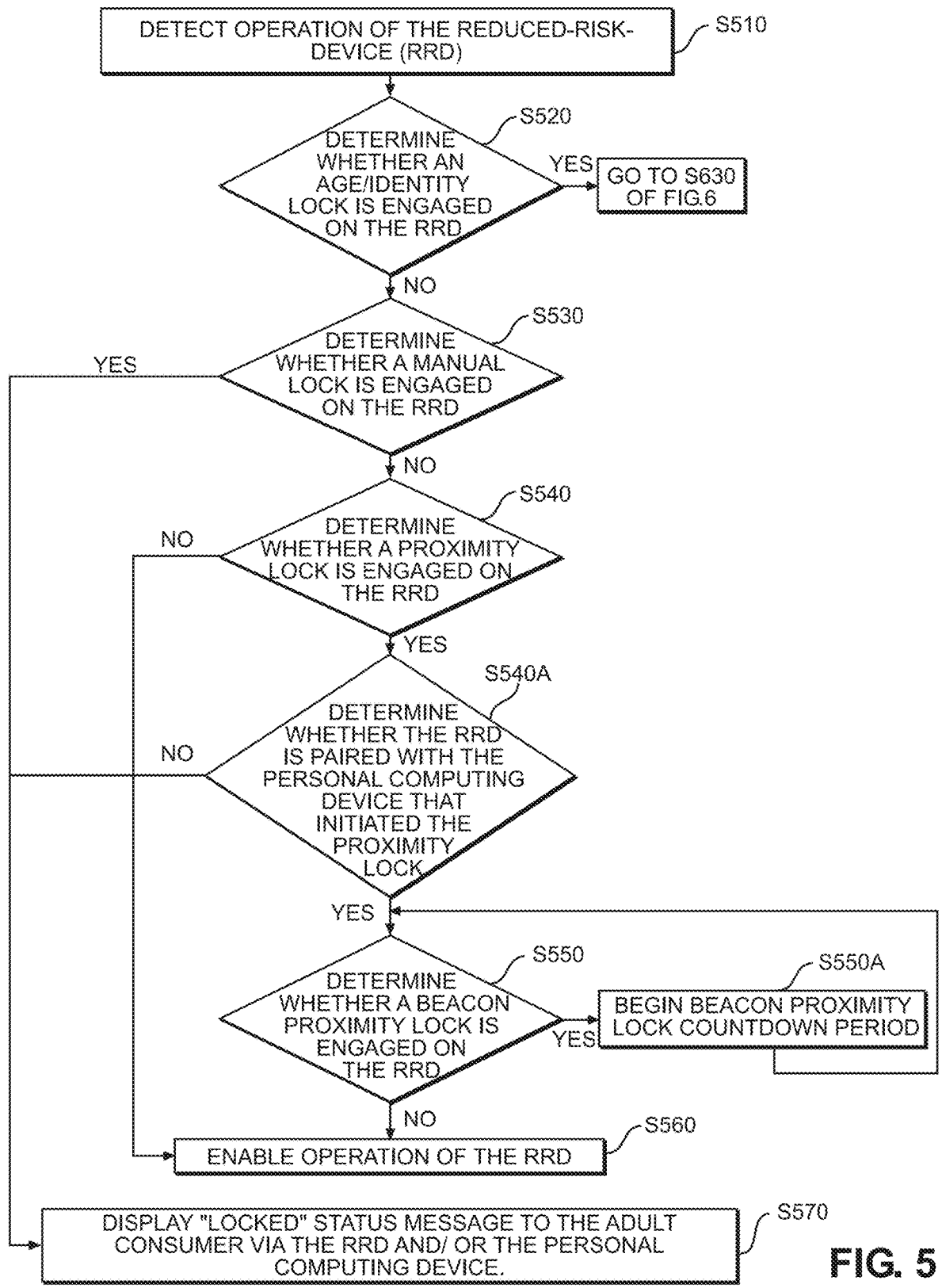
FIG. 5 is a flowchart illustrating a method for operating a reduced-risk device according to at least one example embodiment.

FIG. 5 is a flowchart illustrating a method for operating a reduced-risk device according to at least one example embodiment.

Referring to FIG. 5, a method for operating a reduced-risk device according to at least one example embodiment is shown, however the example embodiments are not limited thereto. In operation S510, the reduced-risk device may detect the beginning of the operation of the reduced-risk device based on, for example, negative air pressure applied to the mouthpiece of the reduced-risk device using the puff sensor, the engagement of the power button (e.g., on/off button, etc.), a request (e.g., a wireless pairing request (e.g., Bluetooth pairing request, NFC pairing request, WiFi pairing request, etc.), an age/identity verification request, etc.) transmitted from the reduced-risk device software, etc.

In operation S520, the reduced-risk device may determine whether an age/identity lock has been engaged (e.g., a first lock, the reduced-risk device is in the lock state, and/or the age/identity lock flag has been set, etc.) on the reduced-risk device based on the settings stored in the memory of the reduced-risk device (e.g., the lock control routine 523 of the memory). In response to the reduced-risk device determining that the age/identity lock has been engaged, the reduced-risk device may perform an age/identity verification method according to some example embodiments, such as the operations starting at operation S630 of FIG. 6, but are not limited thereto. The age/identity verification method is discussed in further detail in FIG. 6.

In response to the reduced-risk device determining that the age/identity lock has not been engaged, in operation S530, the reduced-risk device may determine whether a manual lock (e.g., a second lock, etc.) has been engaged based on the settings stored in the memory of the reduced-risk device (e.g., the lock control routine 523 of the memory).

In response to the reduced-risk device determining that the manual lock has been engaged, the reduced-risk device proceeds to operation S570. In response to the reduced-risk device determining that the manual lock has not been engaged and/or disengaged (e.g., a second manual lock instruction has been received from the personal computing device that sent the first manual lock instruction that placed the reduced-risk device in the manual lock state), in operation S540, the reduced-risk device may determine whether a proximity lock (e.g., a third lock, etc.) has been engaged based on the settings stored in the memory of the reduced-risk device (e.g., the lock control routine 523 of the memory).

In response to the reduced-risk device determining that the proximity lock has not been engaged, the reduced-risk device proceeds to operation S550. In response to the reduced-risk device determining that the proximity lock has been engaged, the reduced-risk device determines whether it is connected to the same personal computing device that initially set the proximity lock (e.g., the personal computing device that transmitted the initial proximity lock instruction, the personal computing device that initiated the proximity lock, etc.) based on a personal computing device UID included in the initial proximity lock instruction (e.g., a unique serial number associated with the personal computing device and/or the reduced-risk device software installed on the personal computing device, an IP address and/or MAC address associated with the personal computing device, a UID associated with the adult consumer, a UID associated with the reduced-risk device software installed on the personal computing device, a connection session ID corresponding to the communication session established between the personal computing device and the reduced-risk device, etc.) and stored in the memory of the reduced-risk device (e.g., stored in the lock control routine 523 of the memory), and a personal computing device UID received from the personal computing device that is connected to (e.g., paired with) the reduced-risk device (e.g., received in a second proximity lock instruction, received upon the wireless pairing of the personal computing device and the reduced-risk device, etc.). In response to the personal computing device UIDs not matching (and/or a personal computing device not being paired with the reduced-risk device), the reduced-risk device remains in the proximity lock state, the operation of the reduced-risk device remains prohibited, and the reduced-risk device proceeds to operation S470. However, in response to the personal computing device UIDs of the initial proximity lock instruction and the currently paired personal computing device matching, the reduced-risk device changes the state of the proximity lock to the unlocked state and proceeds to operation S550.

In operation S550, the reduced-risk device may determine whether a beacon proximity lock (e.g., a fourth lock, etc.) has been engaged based on the settings stored in the memory of the reduced-risk device (e.g., the lock control routine 523 of the memory). In response to the reduced-risk device determining that the beacon proximity lock has been engaged (e.g., that a beacon proximity lock instruction has been received from a wireless beacon transmitter, etc.), the reduced-risk device proceeds to operation S550A and starts a countdown timer of a desired length of time. When the countdown timer expires and no additional beacon proximity lock instructions have been received from the wireless beacon transmitter and/or the reduced-risk device is no longer within the range of the wireless beacon transmitter, the reduced-risk device disengages the beacon proximity lock (e.g., sets the beacon proximity status to the unlocked state, etc.) and repeats operation S550. If the reduced-risk device receives another beacon proximity lock instruction while the countdown timer is running, the state of the beacon proximity lock remains in the locked state, and the countdown timer is reset and restarts. Additionally, if the reduced-risk device receives a beacon proximity lock instruction while in the beacon proximity lock is in the unlocked state, the reduced-risk device immediately changes the state of the beacon proximity lock state to the locked state, disables the operation of the reduced-risk device (if the reduced-risk device was being operated at the time), and begins the countdown timer.

In response to the beacon proximity lock being disengaged, the reduced-risk device proceeds to operation S560. In operation S560, the reduced-risk device enables the operation of the reduced-risk device by the adult consumer, e.g., by enabling the power supply of the reduced-risk device to supply power to the heating coil of the reduced-risk device.

Additionally, in response to the reduced-risk device determining that one or more of the age/identity lock, manual lock, the proximity lock, and/or the beacon proximity lock has been engaged, the reduced-risk device performs operation S570 and may display a "Locked" status message to the adult consumer via the user interface of the reduced-risk device and/or via the GUI of the reduced-risk device software on the personal computing device. For example, the "Locked" status message may also include a message indicating which lock(s) are engaged so that the adult consumer may disengage the appropriate lock to enable operation of the reduced-risk device, but the example embodiments are not limited thereto.

Additionally, the example embodiments are not limited as described above, and for example, the number of locks provided by the reduced-risk device may be a greater number or lesser number than discussed herein. Further, the example embodiments are not limited to the order of operations described above, and the ordering of the operations may be changed as desired by one of ordinary skill in the art.

Figure 6:
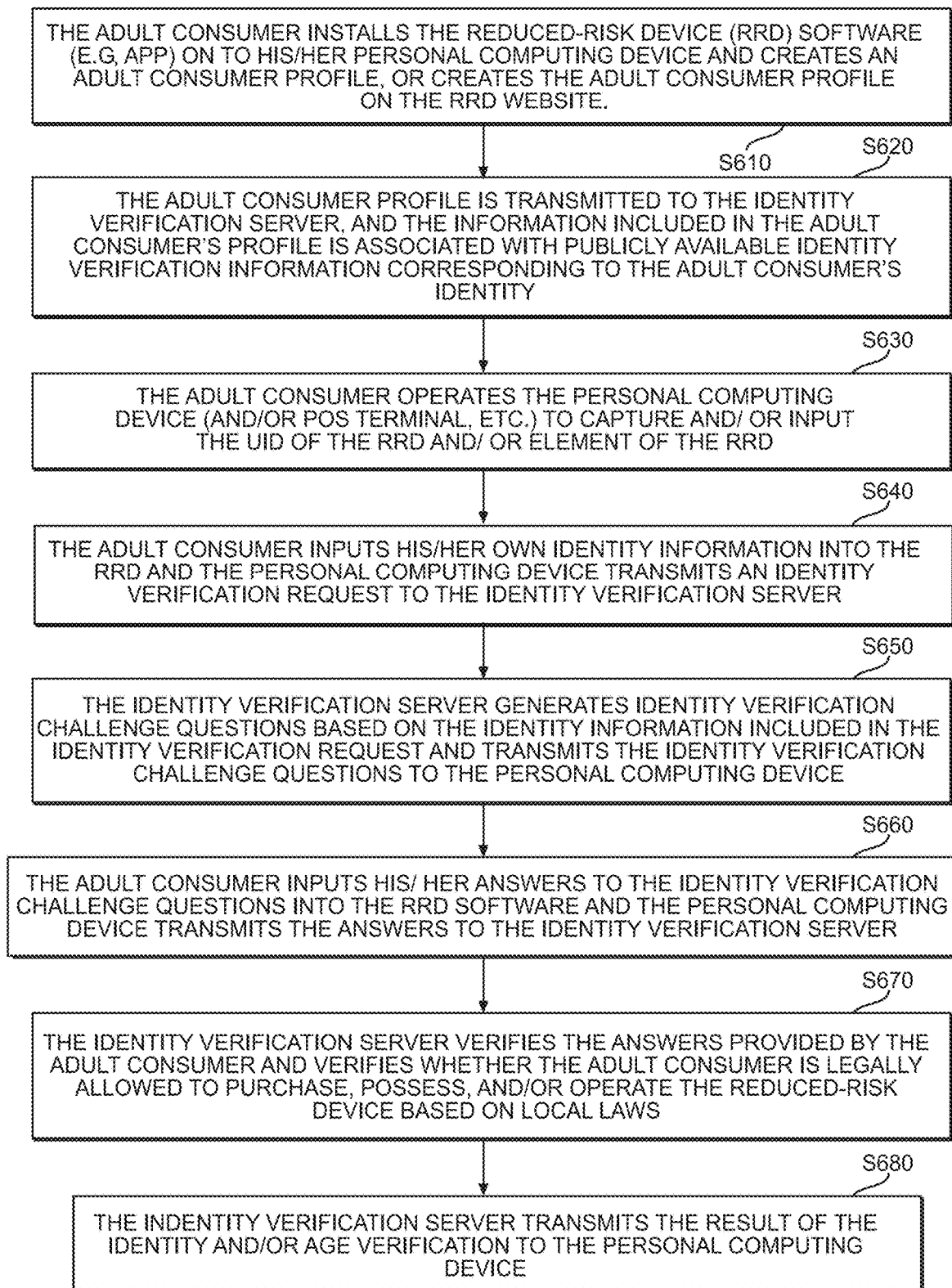
FIG. 6 is a flowchart illustrating a method for verifying an age and/or identity of an adult consumer associated with a reduced-risk device according to at least one example embodiment.

FIG. 6 is a flowchart illustrating a method for verifying an age and/or identity of an adult consumer associated with a reduced-risk device according to at least one example embodiment.

Referring to FIG. 6, a method for verifying an age and/or identity of an adult consumer associated with a reduced-risk device according to at least one example embodiment is shown, however the example embodiments are not limited thereto. In operation S610, an adult consumer may install a reduced-risk device software application (e.g., app, etc.) on his or her personal computing device (e.g., smartphone, tablet, laptop, personal computer, smartwatch, VR device, AR device, etc.). Additionally, the adult consumer may create an adult consumer profile using the reduced-risk device software and/or a website associated with the identity verification server and/or the third-party identity verification service. The adult consumer profile may include information such as, the legal name of the adult consumer, birthdate of the adult consumer, address information of the adult consumer (e.g., street address, mailing address, business address, etc.), government issued identification numbers associated with the adult consumer, such as a Social Security Number of the adult consumer, driver's license number of the adult consumer, passport number of the adult consumer, etc., contact information of the adult consumer (e.g., a phone number, email address, SNS information, IM information, etc.), biometric information of the adult consumer (e.g., fingerprint of the adult consumer, voice signature of the adult consumer, facial recognition signature of the adult consumer, retinal signature of the adult consumer, heart beat signature of the adult consumer, etc.), however, the example embodiments are not limited thereto. Additionally, the adult consumer profile information may also include an adult consumer-created password, PIN information, etc., for securing the adult consumer profile, and/or may also include adult consumer-created identity verification challenge questions for future authentication of the age/identity of the adult consumer and the adult consumer-provided answers to the adult consumer-created identity verification challenge questions. Moreover, according to some example embodiments, the adult consumer profile information may be stored on the personal computing device and/or website in encrypted form.

In operation S620, the adult consumer profile (e.g., adult consumer profile information) stored on the personal computing device and/or website may be transmitted to the identity verification server. The identity verification server may store the adult consumer profile in its memory in an encrypted form, and may associate the adult consumer profile with publicly available identity verification information corresponding to the adult consumer's identity. For example, the identity verification server may associate the adult consumer profile with information obtained from the third-party identity verification service, governmental databases, credit agencies, etc., including information such as, past addresses associated with the adult consumer's identity, past phone numbers associated with the adult consumer's identity, family member information associated with the adult consumer's identity, biographical information related to the adult consumer's identity (e.g., place of birth, hospital that the adult consumer was born, foreign countries visited, information related to the adult consumer's spouse, partner, children, parents, other relatives, etc.), educational history information associated with the adult consumer's identity (e.g., schools attended by the adult consumer, graduation dates associated with the adult consumer, awards received while attending school, etc.), banking/financial history of the adult consumer, employment history of the adult consumer, etc., however the example embodiments are not limited thereto. Additionally, the identity verification server may assign a UID associated with the adult consumer profile.

In operation S630, the adult consumer may operate the personal computing device (and/or the POS terminal, etc.) to capture the UID of the reduced-risk device and/or the UID of the elements of the reduced-risk device, such as the dispersion generating article, etc., using the camera and/or sensors of the personal computing device, or the POS terminal. Alternatively, the adult consumer may input the UID manually using the GUI of the reduced-risk device software.

In operation S640, the adult consumer may input his or her identity information (e.g., name, etc.) into the reduced-risk device software, and the personal computing device or the POS terminal may transmit an identity verification request to the identity verification server, the request including the adult consumer identity information and the UID of the reduced-risk device and/or elements of the reduced-risk device that need to be unlocked. Additionally, other information may be included in the identity verification request, such as location information associated with the personal computing or the POS terminal transmitting the identity verification request, IP address and/or MAC address of the personal computing device and/or POS terminal associated with the verification request, retail store information (e.g., a store number, store location information, identity of the retail employee assisting the adult consumer with the purchase of the reduced-risk device, etc.) associated with the POS terminal if the POS terminal transmits the identity verification request, etc.

In operation S650, the identity verification server may receive the identity verification request from the personal computing device or the POS terminal, and may generate at least one identity verification challenge question for verifying the identity and/or the age of the adult consumer, and corresponding answer, based on the information included in the identity verification request, the adult consumer profile information stored on the identity verification server, and/or information received from the third-party identity verification service. For example, the identity verification server may generate identity verification challenge questions related to the adult consumer's mother's maiden name, place of birth, employment history, educational history, banking/financial history, places that the individual has lived, names of relatives, etc. The identity verification challenge questions may be questions that the adult consumer has previously created and/or submitted answers for that were stored in the adult consumer profile, such as entry of a password or PIN previously created by the adult consumer, adult consumer-created identity challenge questions, etc. Additionally, according to some example embodiments, the identity verification server may request identity verification questions, and corresponding answers, be generated by the third-party identification service (e.g., an external identity verification service, a government identity verification service, etc.) based on public records available related to the adult consumer. Further, the identity verification server may generate identity verification challenge questions requesting the adult consumer provide biometric information (e.g., fingerprints, facial scan, retina scan, voice identification, etc.) that matches previously provided biometric information of the adult consumer stored in the adult consumer profile. However, the example embodiments are not limited thereto and the identity verification challenge questions may take other equivalent forms that provide accurate verification of a person's identity. Once the identity identification challenge questions have been generated, the identity verification server may transmit the questions to the personal computing device or POS terminal that initially transmitted the identity verification request.

In operation S660, the personal computing device or POS terminal receives the generated identity verification challenge questions from the identity verification server, and presents the questions to the adult consumer (e.g., displays the questions, audibly announces the questions, etc.), and receives an answer to the questions from the adult consumer. For example, the adult consumer may type their answer, speak their answer, provide their biometric information, etc., into the personal computing device or POS terminal. The personal computing device or POS terminal may then transmit the answer to the identity verification server.

In operation S670, the identity verification server may verify the received identity verification answer based on the information corresponding to the adult consumer previously stored in the adult consumer profile and/or provided by the third party identity verification service, etc., and determine whether the received identity verification answer matches the answer to the identity verification question generated by the identity verification server (and/or stored on the identity verification server). Additionally, assuming the identity verification attempt was successful, the identity verification server may also determine the age of the adult consumer based on the information stored in the adult consumer profile, and determine whether the adult consumer is legally allowed to purchase, possess, and/or operate the reduced-risk device and/or elements of the reduced-risk device based on the location information included with the identity verification request, the address information associated with the adult consumer in the adult consumer profile, the retail store location information, etc., and the relevant laws of the jurisdiction corresponding to the location information. In the event that the adult consumer successfully verified his or her identity based on the identity challenge questions and the age associated with the adult consumer is determined to satisfy all legal requirements related to the reduced-risk device, the identity verification server determines that the identity and/or age verification request was successful. However, in the event that the adult consumer successfully verified his or her identity based on the identity challenge questions, but the age requirement is not determined to be successful, and/or the adult consumer failed to successfully verify his or her identity, then the identity verification server determines that the identity and/or age verification request was unsuccessful/failed.

In operation S680, the identity verification server transmits the results of the identity and/or age verification to the personal computing device or the POS terminal. According to some example embodiments, the identity verification server may generate an encrypted key for unlocking the reduced-risk device and/or elements of the reduced-risk device based on the verification result and a public key stored on the identity verification server (such as a public key associated with the reduced-risk device, a public key associated with the adult consumer, and/or other public key, etc.), the UID of the reduced-risk device, and/or the personal UID of the adult consumer, etc., however the example embodiments are not limited thereto, and the encrypted key may also be generated based on other information as well. For example, the public key may be the UID of the reduced-risk device 310, etc. The identity verification server may then transmit the encrypted key to the personal computing device or the POS terminal in lieu of transmitting the verification results.

Additionally, according to some example embodiments, the identity verification server may log the verification attempts in a database, such as the verification information database 623. For example, the identity verification server may log all verification attempts, or may log only unsuccessful verification attempts. Data included in the verification attempt logs may include the date, time, adult consumer identity used in the verification attempt, result of the verification attempt, UID of the reduced-risk device and/or element of the reduced-risk device corresponding to the verification attempt, IP address and/or MAC address of the personal computing device and/or POS terminal associated with the identity verification request, location information (e.g., GPS information, latitude/longitude, street address associated with the POS terminal, etc.) associated with the personal computing device and/or POS terminal associated with the verification attempt, store/retail employee information associated with the point-of-sale of the reduced-risk device, etc., but the example embodiments are not limited thereto, and other information may also be logged. Further, if the number of unsuccessful verification attempts exceeds a desired threshold number (e.g., the desired threshold number may be any number greater than or equal to one), information related to unsuccessful verification attempts may be forwarded to relevant authorities, such as governmental agencies (e.g., law enforcement, public health officials, state regulators, etc.), school officials, employers, etc., so that possible illegal activity related to the sale or consumption of reduced-risk devices to minors, etc., may be monitored and/or remediated. Additionally, information related to unsuccessful verification attempts may also be forwarded to an address (e.g., mailing address, email address, phone number, etc.) associated with the identity of the adult consumer that the request attempted to verify, etc., so that the authentic adult consumer may be informed of unsuccessful attempts to use the adult consumer's identity to pass an age/identity verification for the unlocking of a reduced-risk device. Moreover, if the number of unsuccessful verification attempts exceeds the desired threshold number, then the adult consumer may be permanently blocked from being able to use the identity verification service (e.g., subsequent attempts to use the adult consumer's identity with the identity verification service may automatically be rejected by the identity verification server), and/or the identity verification server may transmit a permanent lock instruction to the reduced-risk device software installed on the personal computing device and/or to the reduced-risk device itself.

Figure 7:
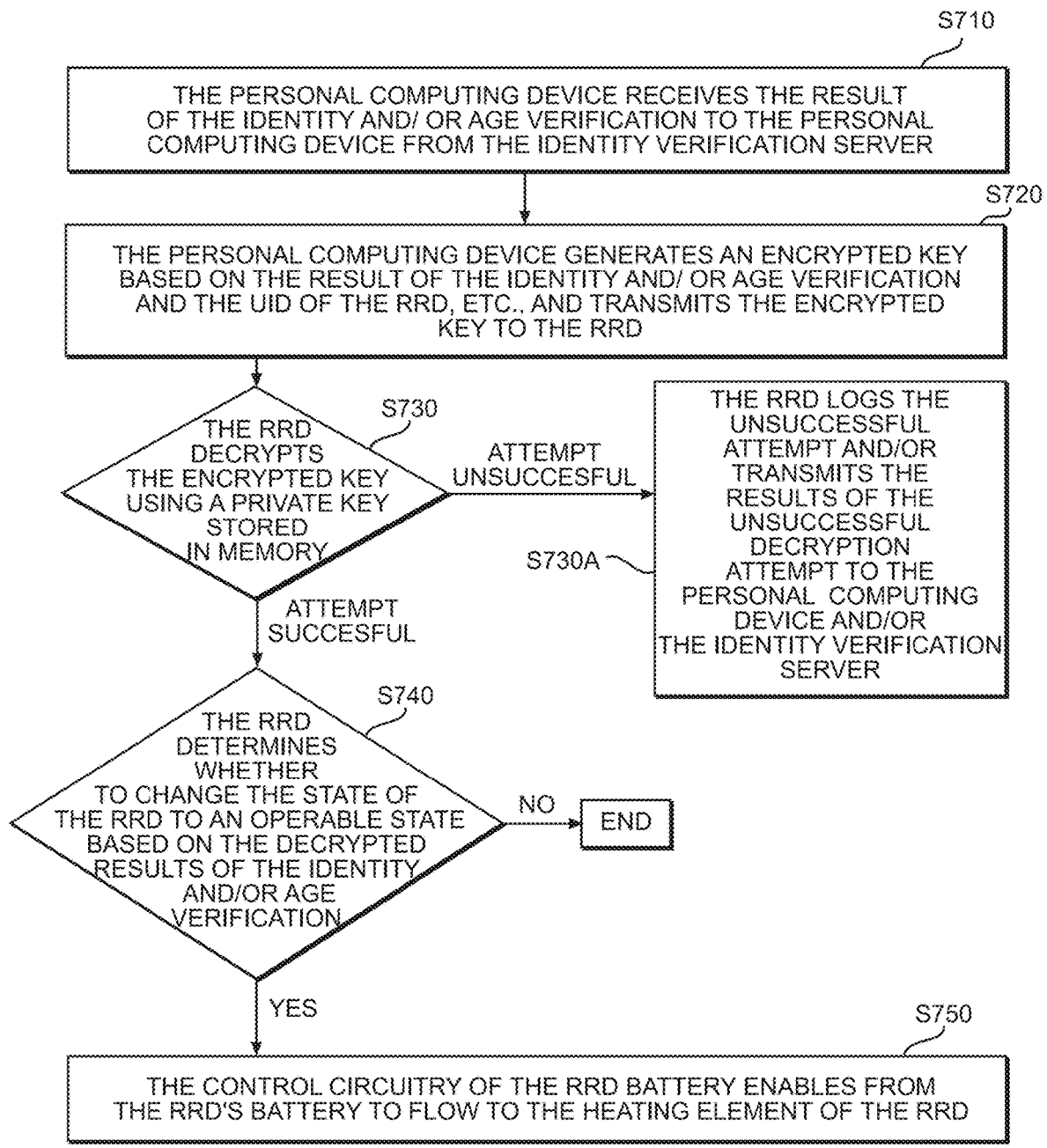
FIG. 7 is a flowchart illustrating a method for unlocking a locked reduced-risk device based on results of an age and/or identity verification request according to at least one example embodiment.

FIG. 7 is a flowchart illustrating a method for unlocking a locked reduced-risk device based on results of an age and/or identity verification request according to at least one example embodiment.

In operation S710, the personal computing device (or POS terminal) that initiated the age and/or identity verification request receives the results of the identity verification performed by the identity verification server from the identity verification server. In operation S720, the personal computing device (or POS terminal) may generate an encrypted key for unlocking the locked reduced-risk device (and/or the locked elements of the reduced-risk device) based on the verification results. For example, the encrypted key based on a public key stored on the personal computing device (such as a public key associated with the reduced-risk device, a public key associated with the adult consumer, and/or other public key, etc.), the UID of the reduced-risk device, the personal UID of the adult consumer, and/or the verification result, etc., however the example embodiments are not limited thereto and the encrypted key may also be generated based on other information as well. Alternatively, according to some example embodiments, the personal computing device (or the POS terminal) may receive identity verification results from the identity verification server which may include an encrypted key that was generated by the identity verification server.

Additionally, the personal computing device may transmit the encrypted key to the reduced-risk device.

Alternatively, according to some example embodiments, the POS terminal may transmit the encrypted key to the reduced-risk device over a wireless and/or wired communication channel, if the reduced-risk device has been removed from its packaging. Additionally, the POS terminal may unlock the reduced-risk device by emitting pressurized bursts of air of a desired air pressure and/or frequency to the puff sensor of the reduced-risk device which corresponding to the encrypted key. Further, the POS terminal may emit a coded sound corresponding to the encrypted key through a speaker, which is received by a microphone of the reduced-risk device.

In operation S730, the reduced-risk device may decrypt the encrypted key using a private key stored on the memory of the reduced-risk device. The reduced-risk device may decrypt the encrypted key using a private key corresponding to the public key used to encrypt the encrypted key. For example, the private key may be a key stored on the reduced-risk device that corresponds to the UID of the reduced-risk device, etc. Additionally, in the event that the reduced-risk device is unable to decrypt the encrypted key using the private key, such as in the event that an attempt at circumventing the identity verification is performed using an encrypted key copied from a previous successful identity verification attempt, etc., the reduced-risk device may log the unsuccessful decryption attempt and/or transmit the results of the unsuccessful decryption attempt to the personal computing device (or POS terminal) and/or the identity verification server for further logging.

In operation S740, the reduced-risk device may determine whether the adult consumer was properly verified and/or is legally permitted to operate the locked reduced-risk device and/or the locked elements of the reduced-risk device, based on the verification results included in the decrypted key. If the verification results indicate the adult consumer is properly verified, the reduced-risk device may unlock the reduced-risk device and/or the locked element(s) of the reduced-risk device (e.g., enable the operation of the reduced-risk device, the dispersion generating article, the power supply, etc., of the reduced-risk device). The locked reduced-risk device and/or the locked element(s) of the reduced-risk device may be unlocked for an indeterminate period of time (e.g., permanently unlocked), may be unlocked for a desired period of time (e.g., temporarily unlocked for 15 minutes, 30 minutes, etc.), and/or may be unlocked while a desired unlock condition is satisfied.

In operation S750, in response to the reduced-risk device being changed to the operable state, the control circuitry of the reduced-risk device enables operation of the reduced-risk device, such as enabling current to flow from the reduced-risk device's battery to the heating element of the reduced-risk device, enabling the operation of a dispersion generating article, etc., and/or other operations.

According to one or more of the example embodiments, an identity verification system, apparatus, method, and/or non-transitory computer readable medium is provided that improves the process of verifying the age of a purchaser of a tobacco-related, nicotine-related, and/or non-nicotine related products at a time of sale, such as nicotine and/or non-nicotine versions of reduced-risk or reduced-harm devices, e.g., heat-not-burn aerosol generating devices, non-heated inhalable aerosol generating devices, and/or e-vaping devices, etc. Additionally, one or more of the example embodiments provide identity verification services at the time that an individual attempts to operate a reduced-risk device (and/or reduced-harm device), and does not permit operation of the reduced-risk device if the individual's age and/or identity is not verified. Further, one or more of the example embodiments allow an adult consumer to manually lock a reduced-risk device to reduce and/or eliminate the possibility that an unauthorized person operates the reduced-risk device. Also, one or more of the example embodiments enable an adult consumer to locate a reduced-risk device that has been lost based on the location that the reduced-risk device was last operated, which also reduces and/or eliminates the possibility that an unauthorized person operates the reduced-risk device.

It should be understood that when an element or layer is referred to as being "on," "connected to," "coupled to," or "covering" another element or layer, it may be directly on, connected to, coupled to, or covering the other element or layer or intervening elements or layers may be present. In contrast, when an element is referred to as being "directly on," "directly connected to," or "directly coupled to" another element or layer, there are no intervening elements or layers present. Like numbers refer to like elements throughout the specification. As used herein, the term "and/or" includes any and all combinations of one or more of the associated listed items.

It should be understood that, although the terms first, second, third, or the like, may be used herein to describe various elements, modules, regions, layers and/or sections, these elements, modules, regions, layers, and/or sections should not be limited by these terms. These terms are only used to distinguish one element, module, region, layer, or section from another region, layer, or section. Thus, a first element, module, region, layer, or section discussed below could be termed a second element, module, region, layer, or section without departing from the teachings of example embodiments.

Spatially relative terms (e.g., "beneath," "below," "lower," "above," "upper," and the like) may be used herein for ease of description to describe one element or feature's relationship to another element(s) or feature(s) as illustrated in the figures. It should be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the term "below" may encompass both an orientation of above and below. The device may be otherwise oriented (rotated 90 degrees or at other orientations) and the spatially relative descriptors used herein interpreted accordingly.

The terminology used herein is for the purpose of describing various example embodiments only and is not intended to be limiting of example embodiments. As used herein, the singular forms "a," "an," and "the" are intended to include the plural forms as well, unless the context clearly indicates otherwise. It will be further understood that the terms "includes," "including," "comprises," and/or "comprising," when used in this specification, specify the presence of stated features, integers, steps, operations, elements, and/or modules, but do not preclude the presence or addition of one or more other features, integers, steps, operations, elements, modules, and/or groups thereof.

Example embodiments are described herein with reference to cross-sectional illustrations that are schematic illustrations of idealized embodiments (and intermediate structures) of example embodiments. As such, variations from the shapes of the illustrations as a result, for example, of manufacturing techniques and/or tolerances, are to be expected. Thus, example embodiments should not be construed as limited to the shapes of regions illustrated herein but are to include deviations in shapes that result, for example, from manufacturing.

Unless otherwise defined, all terms (including technical and scientific terms) used herein have the same meaning as commonly understood by one of ordinary skill in the art to which example embodiments belong. It will be further understood that terms, including those defined in commonly used dictionaries, should be interpreted as having a meaning that is consistent with their meaning in the context of the relevant art and will not be interpreted in an idealized or overly formal sense unless expressly so defined herein.

Example embodiments have been disclosed herein, it should be understood that other variations may be possible. Such variations are not to be regarded as a departure from the spirit and scope of the present disclosure, and all such modifications as would be obvious to one skilled in the art are intended to be included within the scope of the following claims.

What is claimed is:

1. A computing device for verifying an age and identity of an adult consumer, the computing device comprising:
   a memory having computer readable instructions stored thereon; and
   at least one processor configured to execute the computer readable instructions to,
      receive adult consumer identity information corresponding to the adult consumer from the adult consumer,
      receive a unique ID (UID) of a reduced-risk device (RRD), the UID of the RRD being a public key corresponding to the RRD,
      transmit the adult consumer identity information to an identity verification server to perform age and identity verification of the adult consumer, the transmitting causing the identity verification server to verify an age and identity of the adult consumer based on the adult consumer identity information,
      receive results of the performed age and identity verification from the identity verification server,
      generate an encrypted key corresponding to the RRD based on the results of the performed age and identity verification of the adult consumer and the UID of the RRD, and
      transmit the encrypted key to the RRD, the encrypted key causing the RRD to decrypt the encrypted key using a private key stored in a memory of the RRD, the private key corresponding to the public key, and change an operating state of the RRD to an operable state based on the decrypted key.

2. The computing device of claim 1, wherein the computing device is at least one of a smartphone, a tablet, a laptop, a personal computer, a point-of-sale (POS) terminal, an air puff generator device, or any combinations thereof.

3. The computing device of claim 1, wherein
   the adult consumer identity information includes at least a name of the adult consumer, a birth date of the adult consumer, and a mailing address of the adult consumer; and
   the at least one processor is further configured to,
      transmit the name of the adult consumer, the birth date of the adult consumer, and the mailing address of the adult consumer to the identity verification server via an encrypted communication channel, and
      receive the results of the performed age and the identity verification of the adult consumer via the encrypted communication channel.

4. The computing device of claim 1, wherein
   the UID of the RRD is embodied in at least one of a barcode, a QR code, a NFC tag, a Bluetooth tag, a RFID tag, a magnetic tag, a printed serial number, or a combination thereof.

5. The computing device of claim 1, wherein the at least one processor is further configured to:
   receive a unique ID (UID) of a dispersion generating article for the RRD, the dispersion generating article configured to contain a pre-dispersion formulation;
   generate a second encrypted key corresponding to the dispersion generating article based on the results of the performed age and identity verification of the adult consumer and the UID of the dispersion generating article; and
   transmit the second encrypted key corresponding to the dispersion generating article to the RRD, wherein the second encrypted key causes the RRD to operate the dispersion generating article.

6. A reduced-risk device (RRD) for use with an age and identity verification service, an operating state of the RRD initially being in an inoperable state, the RRD comprising:
   at least one transceiver configured to communicate with at least one computing device;
   a memory configured to store a private key corresponding to the RRD; and
   control circuitry configured to,
      receive an encrypted key corresponding to the RRD from a computing device associated with an adult consumer, the encrypted key generated based on a unique ID (UID) corresponding to the RRD and results of an age and identity verification performed on the adult consumer by an identity verification server, the UID of the RRD being a public key corresponding to the private key,
      decrypt the encrypted key using the private key,
      determine whether the age and the identity of the adult consumer was successfully verified based on the decrypted key, and
      change the operating state of the RRD from the inoperable state to an operable state based on results of the determining whether the age and the identity of the adult consumer was successfully verified.

7. The RRD of claim 6, wherein
   the UID of the RRD is embodied in at least one of a barcode, a QR code, a NFC tag, a Bluetooth tag, a RFID tag, a magnetic tag, a printed serial number, or any combinations thereof; and
   the control circuitry is further configured to change the operating state of the RRD to the operable state in response to the results of the determination indicating the adult consumer meets a legal age requirement for operating the RRD.

8. The RRD of claim 6, wherein the control circuitry is further configured to:
   block current from flowing from a power supply included in the RRD to a heater included in the RRD in response to the operating state of the RRD being in the inoperable state; and
   allow current to flow from the power supply to the heater in response to the operating state of the RRD being in the operable state.

9. The RRD of claim 6, wherein in response to the operating state of the RRD being in the operable state, the control circuitry is further configured to:

determine whether the RRD is within a desired distance range of the computing device based on signals received by the transceiver from the computing device; and change the operating state of the RRD to the inoperable state based on results of the determining whether the RRD is within the desired distance range of the computing device.

10. The RRD of claim 6, wherein in response to the operating state of the RRD being in the operable state, the control circuitry is further configured to:
calculate a length of time that the RRD has been in the operable state; and
change the operating state of the RRD to the inoperable state in response to the length of time exceeding a desired threshold operation time.

11. The RRD of claim 6, wherein the control circuitry is further configured to:
change the operating state of the RRD to the inoperable state in response to a wireless shutoff signal received by the at least one transceiver.

12. An age identity verification system comprising:
a reduced-risk device (RRD) including a unique ID (UID) of the RRD, a memory configured to store a private key, and at least one transceiver, wherein an operating state of the RRD is initially in an inoperable state;
an identity verification server configured to perform age and identity verification related to an adult consumer; and
a computing device configured to,
receive adult consumer identity information corresponding to the adult consumer from the adult consumer,
receive the UID of the RRD, the UID of the RRD being a public key corresponding to the RRD,
transmit the adult consumer identity information and the UID of the RRD to the identity verification server to perform age and identity verification of the adult consumer,
receive results of the performed age and identity verification from the identity verification server,
receive an encrypted key corresponding to the RRD based on the results of the performed age and identity verification of the adult consumer, the encrypted key generated based on the UID of the RRD, the UID of the RRE being a public key corresponding to the RRD, and
transmit the encrypted key to the RRD; and
the RRD is further configured to decrypt the encrypted key using the stored private key, the private key corresponding to the public key, and change the operating state of the RRD to an operable state based on the decrypted key.

13. The system of claim 12, wherein
the adult consumer identity information includes at least a birth date of the adult consumer; and
the identity verification server is further configured to,
receive the adult consumer identity information from the computing device via an encrypted communication channel,
perform the age and the identity verification of the adult consumer by verifying the age and the identity of the adult consumer based on the adult consumer identity information, and
transmit the results of the age and identity verification of the adult consumer to the computing device via the encrypted communication channel.

14. The system of claim 12, wherein
the RRD is further configured to,
determine whether the identity of the adult consumer was successfully verified based on the decrypted key, and
change the operating state of the RRD to the operable state based on results of the determination.

15. The system of claim 14, wherein the RRD is further configured to change the operating state of the RRD to the operable state in response to the results of the determination indicating the adult consumer meets a legal age requirement for operating the RRD.

16. The system of claim 12, wherein
the RRD includes control circuitry, a heater, and a power supply; and
the control circuitry is configured to,
block current from flowing from the power supply to the heater in response to the operating state of the RRD being in the inoperable state, and
allow current to flow from the power supply to the heater in response to the operating state of the RRD being in the operable state.

17. The system of claim 12, wherein in response to the operating state of the RRD being in the operable state, the RRD is further configured to:
determine whether the RRD is within a desired distance range of the computing device based on signals received by the transceiver; and
change the operating state of the RRD to the inoperable state based on results of the determining whether the RRD is within the desired distance range of the computing device.

18. The system of claim 12, wherein in response to the operating state of the RRD being in the operable state, the RRD is further configured to:
calculate a length of time that the RRD has been in the operable state; and
change the operating state of the RRD to the inoperable state in response to the length of time exceeding a desired threshold operation time.

19. The system of claim 12, wherein the RRD is further configured to:
receive a wireless shutoff signal; and
change the operating state of the RRD to the inoperable state in response to the received wireless shutoff signal.

20. The system of claim 12, wherein the UID of the RRD is embodied in at least one of a barcode, a QR code, a NFC tag, a Bluetooth tag, a RFID tag, a magnetic tag, a printed serial number, or any combinations thereof.

* * * * *